US008148092B2

(12) United States Patent
Fang et al.

(10) Patent No.: US 8,148,092 B2
(45) Date of Patent: *Apr. 3, 2012

(54) SYSTEM AND METHOD FOR PERFORMING G PROTEIN COUPLED RECEPTOR (GPCR) CELL ASSAYS USING WAVEGUIDE-GRATING SENSORS

(75) Inventors: Ye Fang, Painted Post, NY (US); Ann M. Ferrie, Painted Post, NY (US); Norman H. Fontaine, Painted Post, NY (US); Joydeep Lahiri, Painted Post, NY (US); Po Ki Yuen, Corning, NY (US)

(73) Assignee: Corning Incorporated, Corning, NY (US)

( * ) Notice: Subject to any disclaimer, the term of this patent is extended or adjusted under 35 U.S.C. 154(b) by 327 days.

This patent is subject to a terminal disclaimer.

(21) Appl. No.: 12/469,054

(22) Filed: May 20, 2009

(65) Prior Publication Data

US 2009/0275074 A1    Nov. 5, 2009

Related U.S. Application Data

(62) Division of application No. 11/100,262, filed on Apr. 5, 2005, now abandoned.

(51) Int. Cl.
G01N 33/567    (2006.01)
C12Q 1/02    (2006.01)

(52) U.S. Cl. ......................................... 435/7.21; 435/29

(58) Field of Classification Search .................. None
See application file for complete search history.

(56) References Cited

U.S. PATENT DOCUMENTS

| 4,815,843 | A  | 3/1989  | Tiefenthaler et al. | 356/128 |
| 5,305,074 | A  | 4/1994  | Feldman | 356/345 |
| 5,738,825 | A  | 4/1998  | Rudigier et al. | 422/82.11 |
| 5,830,766 | A  | 11/1998 | Attridge et al. | 436/518 |
| 6,233,471 | B1 | 5/2001  | Berner et al. | 600/345 |
| 6,340,598 | B1 | 1/2002  | Herron et al. | 436/518 |
| 6,707,561 | B1 | 3/2004  | Budach et al. | 356/521 |
| 6,727,071 | B1 | 4/2004  | Dunlay et al. | 435/7.21 |
| 6,818,886 | B2 | 11/2004 | Tiefenthaler | 250/282 |
| 6,867,869 | B2 | 3/2005  | Budach et al. | 356/521 |
| 6,870,630 | B2 | 3/2005  | Budach et al. | 356/521 |
| 6,893,705 | B2 | 5/2005  | Thomas et al. | 428/141 |
| 6,985,664 | B2 | 1/2006  | Caracci et al. | 385/130 |
| 7,064,844 | B2 | 6/2006  | Budach et al. | 356/521 |
| 7,105,347 | B2 | 9/2006  | Fang et al. | 435/455 |
| 7,264,973 | B2 | 9/2007  | Lin et al. | 436/518 |
| 7,286,221 | B2 | 10/2007 | Caracci et al. | 356/300 |
| 7,627,201 | B2 | 12/2009 | Tiefenthaler | 385/12 |
| 2002/0127565 | A1 | 9/2002  | Cunningham et al. | 435/6 |
| 2002/0160534 | A1 | 10/2002 | Herron et al. | 436/518 |
| 2002/0164824 | A1 | 11/2002 | Xiao et al. | 436/524 |
| 2002/0168295 | A1 | 11/2002 | Cunningham et al. | 422/82.05 |
| 2003/0012692 | A1 | 1/2003  | Lemee et al. | 422/57 |
| 2003/0017580 | A1 | 1/2003  | Cunningham et al. | 435/287.2 |
| 2003/0017581 | A1 | 1/2003  | Li et al. | 435/287.2 |
| 2003/0026891 | A1 | 2/2003  | Qiu et al. | 427/58 |
| 2003/0027327 | A1 | 2/2003  | Cunningham et al. | 435/287.2 |
| 2003/0027328 | A1 | 2/2003  | Cunningham et al. | 435/287.2 |
| 2003/0032039 | A1 | 2/2003  | Cunningham et al. | 435/6 |
| 2003/0059855 | A1 | 3/2003  | Cunningham et al. | 435/7.9 |
| 2003/0068657 | A1 | 4/2003  | Lin et al. | 435/7.9 |
| 2003/0077660 | A1 | 4/2003  | Pien et al. | 435/7.1 |
| 2003/0092075 | A1 | 5/2003  | Pepper | 435/7.9 |
| 2003/0113766 | A1 | 6/2003  | Pepper et al. | 435/6 |
| 2003/0124516 | A1 | 7/2003  | Chung et al. | 435/5 |
| 2003/0138208 | A1 | 7/2003  | Pawlak et al. | 385/37 |
| 2003/0194755 | A1 | 10/2003 | Schnabel et al. | 435/7.23 |
| 2003/0211461 | A1 | 11/2003 | Kariv et al. | 435/4 |
| 2004/0009540 | A1 | 1/2004  | Soohoo et al. | 435/7.23 |
| 2004/0023310 | A1 | 2/2004  | Kariv et al. | 435/7.2 |
| 2004/0023391 | A1 | 2/2004  | Fang et al. | 435/458 |
| 2004/0033539 | A1 | 2/2004  | Schnabel et al. | 435/7.21 |
| 2004/0053209 | A1 | 3/2004  | Kariv et al. | 435/4 |
| 2004/0091397 | A1 | 5/2004  | Picard et al. | 472/99 |
| 2004/0132172 | A1 | 7/2004  | Cunningham et al. | 435/287.2 |
| 2004/0132214 | A1 | 7/2004  | Lin et al. | 436/518 |

(Continued)

FOREIGN PATENT DOCUMENTS

| WO | WO01/57530    | 8/2001 |
| WO | WO02/08762    | 1/2002 |
| WO | WO2004/044171 | 5/2004 |
| WO | WO 2005/017507 | 2/2005 |
| WO | WO2006/107967 | 10/2006 |
| WO | WO2007/015878 | 2/2007 |
| WO | WO2007/018872 | 2/2007 |

OTHER PUBLICATIONS

Hug, T. S., et al., "Optical waveguide lightmode spectroscopy as a new method to study adhesion of anchorage-dependent cells as an indicator of metabolic state", Biosensors & Bioelectronics 16 (2001), p. 865-874.

(Continued)

*Primary Examiner* — Rebecca Prouty
*Assistant Examiner* — Paul Martin
(74) *Attorney, Agent, or Firm* — John L. Haack

(57) ABSTRACT

The present invention includes a system and method that uses optical LID biosensors to monitor in real time agonist-induced GPCR signaling events within living cells. Particularly, the present invention includes a system and method for using an optical LID biosensor to screen compounds against a target GPCR within living cells based on the mass redistribution due to agonist-induced GPCR activation. In an extended embodiment, the present invention discloses different ways for self-referencing the optical LID biosensor to eliminate unwanted sensitivity to ambient temperature, pressure fluctuations, and other environmental changes. In yet another extended embodiment, the present invention discloses different ways for screening multiple GPCRs in a single type of cell or multiple GPCRs in multiple types of cells within a single medium solution. In still yet another extended embodiment, the present invention discloses different ways to confirm the physiological or pharmacological effect of a compound against a specific GPCR within living cells.

5 Claims, 10 Drawing Sheets

U.S. PATENT DOCUMENTS

| | | | |
|---|---|---|---|
| 2004/0151626 A1 | 8/2004 | Cunningham et al. | 422/58 |
| 2004/0223881 A1 | 11/2004 | Cunningham et al. | 422/82.05 |
| 2004/0235198 A1 | 11/2004 | Marx et al. | 436/527 |
| 2004/0263841 A1 | 12/2004 | Caracci et al. | 356/300 |
| 2005/0025421 A1 | 2/2005 | Caracci et al. | 385/37 |
| 2005/0070027 A1 | 3/2005 | Gollier et al. | 436/518 |
| 2005/0100904 A1 | 5/2005 | Yoshizato et al. | 435/6 |
| 2005/0158880 A1 | 7/2005 | Ostuni et al. | 438/1 |
| 2005/0236554 A1 | 10/2005 | Fontaine et al. | 250/208.1 |
| 2006/0063276 A1 | 3/2006 | Jiang et al. | 436/518 |
| 2006/0205058 A1 | 9/2006 | Frutos et al. | 435/287.1 |
| 2006/0205092 A1 | 9/2006 | Lackritz et al. | 436/525 |
| 2006/0223051 A1 | 10/2006 | Fang et al. | 435/4 |

OTHER PUBLICATIONS

Ramsden, J. J., "Optical Method for Measurement of Number and Shape of Attached Cells in Real Time", Cytometry 19, 1995, p. 97-102.

Hug, T. S., "Optical Waveguide Lightmode Spectroscopy (OWLS) to Monitor Cell Proliferation Quantitatively", Biotechnology and Bioengineering, vol. 80, No. 2, Oct. 20, 2002, p. 213-221.

Horvath, R., "Optical waveguide sensor for on-line monitoring of bacteria", Optics Letters, Jul. 15, 2003, vol. 28, No. 14, p. 1233-1235.

Hug, T. S., "Biophysical Methods for Monitoring Cell-Substrate Interactions in Drug Discovery", ASSAY and Drug Development Technologies, vol. 1, No. 3, 2003, p. 479-488.

Horvath, R., "Monitoring of living cell attachment and spreading using reverse symmetry waveguide sensing", Applied Physics Letters 86, (2005), 071101-1-071101-3.

Corso, C. D., "An investigation of antibody immobilization methods employing organosilanes on planar ZnO surfaces for biosensor applications", Biosensors and Bioelectronics 24, (2008), p. 805-811.

M. Hide et al., "Real-Time Analysis of Ligand-Induced Cell Surface and Intracellular Reactions of Living Mast Cells Using a Surface Plasmon Resonance-Based Biosensor", Analytical Biochemistry, vol. 302, 2002, pp. 28-37.

D.R. Alessi et al., "PD 098059 Is a Specific Inhibitor of the Activation of Mitogen-activated Protein Kinase Kinase in Vitro and in Vivo", The Journal of Biological Chemistry, Nov. 17, 1995, vol. 270, No. 46, pp. 27489-27494.

M. Azzi et al., "β-Arrestin-mediated activation of MAPK by inverse agonists reveals distinct active conformations for G protein-coupled receptors", PNAS, Sep. 30, 2003. vol. 100, No. 20, pp. 11406-11411.

J.G. Baker et al., "Influence of Agonist Efficacy and Receptor Phosphorylation on Antagonsit Affinity Measurements: Differences between Second Messenger and Reporter Gene Responses", Mol. Pharmacol., 2003, vol. 64, No. 3, pp. 679-688.

Z. Bajzer et al., "Binding, Internalization, and Intracellular Processing of Proteins Interacting with Recycling Receptors", The Journal of Biological Chemistry, Aug. 15, 1989, vol. 264, No. 23, pp. 13623-13631.

D.W. Barnes, "Epidermal Growth Factor Inhibits Growth of A431 Human Epidermoid Carcinoma in Serum-free Cell Culture", The Journal of Cell Biology, Apr. 1982, vol. 93, pp. 1-4.

O. Beske et al., "A Novel Encoded Particle Technology that Enables Simultaneous Interrogation of Multiple Cell Types", The Society of Biomolecular Screening, 2004, vol. 9, No. 3, pp. 173-185.

Brecht et al., "Optical Probes and Transducers*", Biosensors & Bioelectronics, vol. 10, 1995, pp. 923-936.

W. Budach et al., "Planar Waveguides as High-Performance Sensing Platforms for Fluorescence-Based Multiplexed Oligonucleotide Hybridization Assays", Anal. Chem., 1999, vol. 71, pp. 3347-3355.

P. Burke et al., "Regulation of Epidermal Growth Factor Receptor Signaling by Endocytosis and Intracellular Trafficking", Molecular Biology of the Cell, Jun. 2001, vol. 12, pp. 1897-1910.

K. Choudhuri et al., "T-cell receptor triggering is critically dependent on the dimensions of its peptide-MHC ligand", Nature, vol. 436, Jul. 28, 2005, pp. 578-582.

Clerc et al., "Direct Immunosensing With an Integrated-Optical Output Grating Coupler", Sensors & Actuators B, vol. 40, 1997, pp. 53-58.

B. Cunningham et al., "Label-Free Assays on the BIND System", The Society for Biomolecular Screening, 2004, vol. 9, No. 6, pp. 481-490.

R.J. Daly, "Take Your Partners, Please—Signal Diversification by the erbB Family of Receptor Tyrosine Kinases", Growth Factors, vol. 16, pp. 255-263, (1999).

Y. Danjo et al., "Actin 'purse string' filaments are anchored by E-cadherin-mediated adherens junctions at the leading edge of the epithelial wound, providing coordinated cell movement", Journal of Cell Science, 1998, vol. 111, pp. 3323-3331.

H. Daub et al., "Role of transactivation of the EGF receptor in signalling by G-protein-coupled receptors", Nature, Feb. 8, 1996, vol. 379, pp. 557-560.

Drews, "Drug Discovery: A Historical Perspective". Science, Mar. 17, 2000, vol. 287, pp. 1960-1964.

G.L. Duveneck et al., "Novel Bioaffinity Sensors for Trace Analysis Based on Luminescence Excitation by Planar Waveguides", Sensors and Actuators B, vol. 38-39, 1997, pp. 88-95.

G.L. Duveneck et al., "Review on Fluorescence-Based Planar Waveguide Biosensors", Proc. SPIE, vol. 3858, 1999, pp. 59-71.

G.L. Duveneck et al., "Two-Photon Fluorescence Excitation of Macroscopic Areas on Planar Waveguides", Biosensors and Bioelectronics, vol. 18, 2003, pp. 503-510.

P.L. Edmiston et al., "Dipole Orientation Distributions in Langmuir—Blodgett Films by Planar Waveguide Linear Dichroism and Fluorescence Anisotropy", J. Phys. Chem., 1996, vol. 100, pp. 775-784.

Y. Fang, "Label-Free Cell-Based Assays with Optical Biosensors in Drug Discovery", Assay and Drug Development Technologies, vol. 4, No. 5, 2006, pp. 583-595.

Y. Fang et al., "Non-Invasive Optical Biosensor for Assaying Endogenous G Protein-Coupled Receptors in Adherent Cells", Journal of Pharmacological and Toxicological Method, vol. 55, 2007, pp. 314-322.

Y. Fang et al., "Optical biosensor differentiates signalling of endogenous $PAR_1$ and $PAR_2$ in A431 cells", BMC Cell Biology, 2007, vol. 8, No. 24, pp. 1-12, http://www.biomedcentral.com/1471-2121/8/24.

Ye Fang et al., "Optical Biosensor Provides Insights for Bradykinin B2 Receptor Signaling in A431 Cells", FEBS Letters, vol. 579, 2005, pp. 6365-6374.

Y. Fang et al., "Resonant Waveguide Grating Biosensor for Living Cell Sensing", Biophysical Journal, vol. 91, Sep. 2006, pp. 1925-1940.

Y. Fang et al., "G-Protein-Coupled Receptor Microarrays", ChemBioChem, Oct. 4, 2002, vol. 3, No. 10, pp. 987-991.

Ye Fang et al., "Cellular functions of cholesterol probed with optical biosensors", Biochimica et Biophysica ACTA, vol. 1763, 2006, pp. 254-261.

Ye Fang et al., "Probing cytoskeleton modulation by optical biosensor", FEBS Letters, vol. 579. 2005, pp. 4175-4180.

Ye Fang et al., "Characteristics of Dynamic Mass Redistribution of Epidermal Growth Factor Receptor Signaling in Living Cells Measured with Label-Free Optical Biosensors", Anal. Chem., 2005, vol. 77, pp. 5720-5725.

A.R. French et al., "Postendocytic Trafficking of Epidermal Growth Factor-Receptor Complexes Is Mediated Through Saturable and Specific Endosomal Interactions", The Journal of Biological Chemistry, Jun. 3, 1994, vol. 269, No. 22, pp. 15749-15755.

I. Giaever et al., "Monitoring fibroblast behaviour in tissue culture with an applied electric field", Proc. Natl. Acad. Sci., Jun. 1984, vol. 81, pp. 3761-3764.

A. Glading et al., "Epidermal Growth Factor Receptor Activation of Calpain Is Required for Fibroblast Motility and Occurs via an ERK/MAP Kinase Signaling Pathway", The Journal of Biological Chemistry, Jan. 28, 2000, vol. 275, No. 4, pp. 2390-2398.

A. Grakoui et al., "The Immunological Synapse: A Molecular Machine Controlling T Cell Activation", Science, vol. 285. Jul. 9, 1999, pp. 221-227.

H.M. Grandin et al., "Waveguide Excitation Fluorescence Microscopy: A New Tool for Sensing and Imaging the Biointerface", Biosensors and Bioelectronics, vol. 21, 2006, pp. 1476-1482.

A. Graness et al., "Protein-tyrosine-phosphatase-mediated epidermal growth factor (EGF) receptor transinactivation and EGF receptor-independent stimulation of mitogen-activated protein kinase by bradykinin in A431 cells", *Biochem. J.*, 2000, vol. 347, pp. 441-447.

S.A. Green et al., "Sustained Activation of a G Protein-coupled Receptor via "Anchored" Agonist Binding", *The Journal of Biological Chemistry*, vol. 271, No. 39, pp. 24029-24035, (1996).

A. Gschwind et al., "Cell communication networks: epidermal growth factor receptor transactivation as the paradigm for interreceptor signal transmission", *Oncogene*, 2001, vol. 20, pp. 1594-1600.

M. Halter et al., "Enhanced Optical Waveguide Light Mode Spectroscopy Via Detection of Fluorophore Absorbance", *Review of Scientific Instruments*, vol. 77, 2006, pp. 103105-1-6.

W.R. Holland et al., "Waveguide Mode Enhancement of Molecular Fluorescence", *Optics Letters*, vol. 10, No. 8, Aug. 1985, pp. 414-416.

R. Horváth et al., "Effect of patterns and inhomogeneities on the surface of waveguides used for optical waveguide lightmode spectroscopy applications", *Applied Physics B*, 2001, vol. 72, pp. 441-447.

R. Horváth et al., "Reverse-symmetry waveguides: theory and fabrication", *Applied Physics B*, 2002, vol. 74, pp. 383-393.

Y. Huang et al., "Growth Hormone-induced Phosphorylation of Epidermal Growth Factor (EGF) Receptor in 3T3-F442A Cells", *The Journal of Biological Chemistry*, May 23, 2003, vol. 278, No. 21, pp. 18902-18913.

W. Huber et al., "Direct optical immunosensing (sensitivity and selectivity)", *Sensors and Actuators B*, 1992, vol. 6, pp. 122-126.

B. January et al., "$\beta_2$-Adrenergic Receptor Desensitization, Internalization, and Phosphorylation in Response to Full and Partial Agonists", *The Journal of Biological Chemistry*, vol. 272, No. 38, pp. 23871-23879, (1997).

Jin et al., "A Biosensor Concept Based on Imaging Ellipsometry for Visualization of Biomolecular Interactions", Analytical Biochemistry, vol. 232, 1995, pp. 69-72.

Jordan et al., "Surface Plasmon Resonance Imaging Measurements of Electrostatic Biopolymer Adsorption Onto Chemically Modified Gold Surfaces", Anal. Chem., 1997, vol. 69, pp. 1449-1456.

C.E. Jordan et al., "Surface Plasmon Resonance Imaging Measurements of DNA Hybridization Adsorption and Streptavidin/DNA Multilayer Formation at Chemically Modified Gold Surfaces", *Anal. Chem.*, 1997, pp. 4939-4947.

P. Lalanne et al., "Highly Improved Convergence of the Coupled-Wave Method for TM Polarization", *J. Opt. Soc. Am. A*, vol. 13, No. 4, Apr. 1996, pp. 779-784.

M.A. Lemmon et al., "Regulation of signal transduction and signal diversity by receptor oligomerization", *Trends Biochem. Sci.*, 1994, vol. 19, pp. 459-463.

G. Liapakis et al., "Synergistic Contributions of the Functional Groups of Epinephrine to Its Affinity and Efficacy at the $\beta_2$ Adrenergic Receptor", *Mol. Pharmacol.*, 2004, vol. 65, No. 5, pp. 1181-1190.

G. Liapakis et al., "The Forgotten Serine", *The Journal of Biological Chemistry*, vol. 275, No. 48, pp. 37779-37788), (2000).

Y. Liu et al., "Structural basis for selective inhibition of Src family kinases by PP1", *Chemistry & Biology*, 1999, vol. 6, No. 9. pp. 671-678.

E. Livneh et al., "Reconstitution of Human Epidermal Growth Factor Receptors and Its Deletion Mutants in Cultured Hamster Cells", *The Journal of Biological Chemistry*, Sep. 25, 1986, vol. 261, No. 27, pp. 12490-12497.

L. Lorenzelli, et al., "Bioelectrochemical signal monitoring of in-vitro cultured cells by means of an automated microsystem based on solid state sensor-array", *Biosensors and Bioelectronics*, 2003, vol. 18, pp. 621-626.

Z. Lu et al., "Epidermal Growth Factor-Induced Tumor Cell Invasion and Metastasis Initiated by Dephosphorylation and Downregulation of Focal Adhesion Kinase", *Molecular and Cellular Biology*, Jun. 2001, vol. 21, No. 12, pp. 4016-4031.

Morhard et al., "Immobilization of Antibodies in Micropatterns for Cell Detection by Optical Diffraction", Sensors and Actuators B, vol. 70, 2000, pp. 232-242.

K. Mossman et al., "Micropatterned supported membranes as tools for quantitative studies of the immunological synapse", *Chemical Society Reviews*, vol. 36, 2007, pp. 46-54.

B.S. Negrutskii et al., "A sequestered pool of aminoacyl-tRNA in mammalian cells". *Proc. Natl. Acad. Sci. USA*, 1992, vol. 89, pp. 3601-3604.

B.S. Negrutskii et al., "Supramolecular organization of the mammalian translation system", *Proc. Natl. Acad. Sci. USA*, 1994, vol. 91, pp. 964-968.

P.M. Nellen et al., "Integrated Optical Input Grating Couplers as Biochemical Sensors", *Sensors and Actuators*, 1988, vol. 15, pp. 285-295.

Pierce et al., "Seven-Transmembrane Receptors", Nature Reviews, Molecular Cell Biology, vol. 3, Sep. 2002, pp. 639-650.

G. Powis et al., "Wortmannin, a Potent and Selective Inhibitor of Phosphatidylinositol-3-kinase[1]", *Cancer Research*, May 1, 1994, vol. 54, pp. 2419-2423.

Ramsden et al., "Kinetics of Adhesion and Spreading of Animal Cells", Biotechnology and Bioengineering, vol. 43, 1994, pp. 939-945.

H. Resat et al., "An Integrated Model of Epidermal Growth Factor Receptor Trafficking and Signal Transduction", *Biophysical Journal*, Aug. 2003, vol. 85, pp. 730-743.

C. Rosette et al., "Ultraviolet Light and Osmotic Stress: Activation of the JNK Cascade Through Multiple Growth Factor and Cytokine Receptors", *Science*, Nov. 15, 1996, vol. 274, pp. 1194-1197.

M.D. Salik et al., Resonant Excitation Analysis of Waveguide Grating Couplers, *Optics Communications*, vol. 193, Jun. 15, 2001, pp. 127-131.

J. Schlessinger, "Cell Signaling by Receptor Tyrosine Kinases", *Cell*, Oct. 13, 2000, vol. 103, pp. 211-225.

B. Schoeber et al., "Computational modelling of the dynamics of the MAP kinase cascade activated by surface and internalized EGF receptors", *Nature Biotechnology*, Apr. 2002, vol. 20, pp. 370-375.

M.A. Simmons, "Functional Selectivity, Ligand-Directed Trafficking, Conformation-Specific Agonism: What's In A Name?", *Molecular Interventions*, Jun. 2005, vol. 5, Issue 3, pp. 154-157.

"Signal Pathway Identification and Deconvolution", http://www.cellkey.com/apps2.html (accessed Oct. 24, 2008).

E.A. Smith et al., "Surface Plasmon Resonance Imaging as a Tool to Monitor Biomolecular Interactions in an Array Based Format", *Applied Spectroscopy*, 2003, vol. 57. No. 11, pp. 320A-332A.

K. Solly et al., "Application of Real-Time Cell Electronic Sensing (RT-CES) Technology to Cell-Based Assays", *ASSAY and Drug Development Technologies*, 2004, vol. 2, No. 4, pp. 363-372.

G. Swaminath et al., "Probing the $\beta_2$ Adrenoceptor Binding Site with Catechol Reveals Differences in Binding and Activation by Agonists and Partial Agonists", *The Journal of Biological Chemistry*, vol. 280, No. 23, pp. 22165-22171, (2005).

Tiefenthaler et al., "Intregrated Optical Switches and Gas Sensors", Optics Letters, Apr. 1984, vol. 10, No. 4, pp. 137-139.

K. Tiefenthaler at al., "Sensitivity of grating couplers as integrated-optical chemical sensors", *J. Opt. Soc. Am. B*, Feb. 1989, vol. 6, No. 2, pp. 209-220.

P.K. Tien, "Integrated optics and new wave phenomena in optical waveguides", *Reviews of Modern Physics*, Apr. 1977, vol. 49, No. 2, pp. 361-454.

J.D. Urban et al., "Functional Selectivity and Classical Concepts of Quantitative Pharmacology", *The Journal of Pharmacology and Experimental Therapeutics*, vol. 320, No. 1, pp. 1-13, (2007).

E. Verdonk et al., "Cellular Dielectric Spectroscopy: A Label-Free Comprehensive Platform for Functional Evaluation of Endogenous Receptors", *ASSAY and Drug Development Technologies*, 2006, vol. 4, No. 5, pp. 609-619.

P.J. Verveer, et al., "Quantitative Imaging of Lateral ErbB1 Receptor Signal Propagation in the Plasma Membrane", *Science*, Nov. 24, 2000, vol. 290, pp. 1567-1570.

G. Voirin et al., "$Si_3N_4/SiO_2$/Si Waveguide Grating for Fluorescent Biosensors", *Proc. SPIE*, vol. 3620, 1999, pp. 109-116.

J. Vörös et al., "Feasibility study of an online toxicological sensor based on the optical waveguide technique", *Biosensor & Bioelectronics*, 2000, vol. 15, pp. 423-429.

J. Vörös et al., "Optical Grating Coupler Biosensors", *Biomaterials*, vol. 23, 2002, pp. 3699-3710.

Z.H. Wang et al., "A Label-Free Multisensing Immunosensor Based on Imaging Ellipsometry", *Anal. Chem.*, 2003, vol. 75, pp. 6119-6123.

L.C. Waters et al., "Microchip Device for Cell Lysis, Multiplex PCR Amplification, and Electrophoretic Sizing", *Anal. Chem.*, 1998, vol. 70, pp. 158-162.

R. Wetzker et al., "Transactivation joins multiple tracks to the ERK/MAPK cascade", *Nature Reviews Molecular Cell Biology*, Aug. 2003, vol. 4. pp. 651-657.

A.D. Zechnich et al., "Possible Interactions With Terfenadine or Astemizole", *West J. Med.*, Apr. 1994, vol. 160, No. 4, pp. 321-325.

P.N. Zeller et al., "Single-Pad Scheme for Integrated Optical Fluorescence Sensing", *Biosensors & Bioelectronics*, vol. 15, 2000, pp. 591-595.

"Zeptosens—Bioanalytical Solutions", http://www.zeptosens.com/en/ (accessed Oct. 24, 2008).

US 8,148,092 B2

SYSTEM AND METHOD FOR PERFORMING G PROTEIN COUPLED RECEPTOR (GPCR) CELL ASSAYS USING WAVEGUIDE-GRATING SENSORS

CROSS-REFERENCE TO RELATED APPLICATIONS

This application is a divisional application of U.S. patent application Ser. No. 11/100,262, filed Apr. 5, 2005, now abandoned Jun. 10, 2009, the contents of this document are hereby incorporated by reference herein.

BACKGROUND OF THE INVENTION

1. Field of the Invention

The present invention relates in general to the optical non-contact sensor field and, specifically, to a system and method for using an optical label independent detection (LID) biosensor (e.g., waveguide grating-based biosensor) to monitor in real time compound-induced mass redistribution in living cells, including agonist-induced G protein coupled receptor (GPCR) desensitization and translocation within living cells, as well as morphological changes of adherent cells. Particularly, the present invention relates to a system and method for using a LID biosensor to screen compounds against a GPCR within living cells.

2. Description of Related Art

Today an optical-based biosensor like a surface plasmon resonance (SPR) sensor or a waveguide grating-based sensor enables an optical label independent detection (LID) technique to be used to detect a biomolecular binding event at the biosensor's surface. In particular, the optical-based biosensor enables an optical LID technique to be used to measure changes in a refractive index/optical response of the biosensor which in turns enables a biomolecular binding event to be detected at the biosensor's surface. In fact, these optical-based biosensors along with different optical LID techniques have been used to study a variety of biomolecular binding events including oligonucleotides interactions, antibody-antigen interactions, hormone-receptor interactions, and enzyme-substrate interactions (for example).

In general, the optical-based biosensor includes two components: a highly specific recognition element and an optical transducer that converts a molecular recognition event into a quantifiable signal. The traditional studies performed with optical LID techniques have been associated with direct optical methods which include the use of: surface plasmon resonance (SPR) sensors; grating couplers; ellipsometry devices; evanescent wave devices; and reflectometry devices. For a detail discussion about each of these direct optical methods reference is made to the following documents:

Jordan & Corn, "Surface Plasmon Resonance Imaging Measurements of Electrostatic Biopolymer Adsorption onto Chemically Modified Gold Surfaces," Anal. Chem., 1997, 69:1449-1456.

Morhard et al., "Immobilization of antibodies in micropatterns for cell detection by optical diffraction," Sensors and Actuators B, 2000, 70, 232-242.

Jin et al., "A biosensor concept based on imaging ellipsometry for visualization of biomolecular interactions," Analytical Biochemistry, 1995, 232, 69-72.

Clerc and Lukosz "Direct immunosensing with an integrated-optical output grating coupler" Sensors and Actuators B 1997, 40, 53-58.

Brecht & Gauglitz, "Optical probes and transducers," Biosensors and Bioelectronics, 1995, 10, 923-936.

The contents of these documents are incorporated by reference herein.

To date, there have been relatively few reports describing the use of optical LID techniques to perform cell-based assays. For example, SPR biosensors have been used to investigate the adhesion and spreading of animal cells as described in the following document:

J. J. Ramsden, S. Y. Li, J. E. Prenosil and E. Heinzle, "Kinetics of adhension and spreading of animal cells" Biotechnol. Bioeng. 1994, 43, 939-945.

And, SPR biosensors have been used to investigate ligand-induced cell surface and intracellular reactions of living cells as described in the following document:

M. Hide, et al. "Real-time analysis of ligand-induced cell surface and intracellular reactions of living mast cells using a surface plasmon resonance-based biosensor", Anal. Biochem. 2002, 302, 28-37.

However, to date there has been no report concerning the use of optical LID techniques to monitor compound-induced mass redistribution within adherent cells including agonist-induced translocation of G protein coupled receptors (GPCRs) within living cells. It would be desirable if this was possible, because GPCRs, a family of cell surface receptors, are the most common targets that new drug compounds are designed against. And, because GPCRs can transduce exogenous signals (i.e., the presence of stimuli such as a new drug) into intracellular response(s) which makes them extremely valuable in the testing of new drugs.

GPCRs participate in a wide array of cell signaling pathways. Ligand binding initiates a series of intracellular and cellular signaling events, including receptor conformational changes, receptor oligomerization, G protein activation (GDP-GTP exchanges on $G_\alpha$ subunit, $G_\alpha$ and $G_{\beta\gamma}$ disassociation, G protein decoupling from the receptor, generation of $G_\alpha$- and $G_{\beta\gamma}$-signaling complexes), and downstream signaling activation that leads to second messenger generation ($Ca^{2+}$ mobilization, inositoltriphosphate generation, and/or intracellular cAMP level modulation) and ultimately results in changes of specific gene expression. Ligand-mediated GPCR activation also leads to the desensitization of GPCRs from the cell surface and trafficking of many intracellular proteins, as well as changes in phenotypes, morphology and physical properties of the target cells. These changes could be static, long-lasting or dynamic (e.g., cycling or oscillation). Distinct signaling events exhibit significantly different kinetics ranging from milliseconds (e.g., GPCR conformational changes) to tens of seconds (e.g., $Ca^{2+}$ flux) to even tens of minutes (e.g., gene expression, or morphological changes). Current GPCR assays include ligand-receptor binding, second messenger ($Ca^{2+}$, cAMP of IP3) assays, protein interaction assays, translocation assays and reporter gene assays. Since GPCR activation ultimately leads to protein trafficking and/or morphological changes, methods that can study the action of any compounds through the GPCRs on cell surface and the consequent events (e.g., trafficking and/or morphological changes) of the effected cells would be desired. This need and other needs are addressed by the present invention.

BRIEF DESCRIPTION OF THE INVENTION

The present invention includes a system and method that uses optical LID biosensors to monitor in real time compound-induced mass redistribution including agonist-induced GPCR signaling events within living cells. Particularly, the present invention includes a system and method for using an optical LID biosensor to screen compounds against a target GPCR within living cells based on the morphological changes of the cell and/or desensitization and/or translocation of the GPCR. In an extended embodiment, the present invention discloses methods for self-referencing the optical LID biosensor to eliminate unwanted sensitivity to ambient temperature, pressure fluctuations, and other environmental changes, and also methods to provide confirmative information of the compound action on a particular pre-selected target through comparison of the responses of two types of cells spatially separated but located on the same sensor. In yet another extended embodiment, the present invention discloses different ways for screening multiple GPCRs in a single type of cell or multiple GPCRs in multiple types of cells within a single medium solution. In still yet another extended embodiment, the present invention discloses different ways to confirm the physiological or pharmacological effect of a compound against a specific GPCR within living cells.

BRIEF DESCRIPTION OF THE DRAWINGS

A more complete understanding of the present invention may be had by reference to the following detailed description when taken in conjunction with the accompanying drawings wherein:

FIG. 10 is a time-dependent LID response of Chinese Hamster Ovary (CHO) cells before and after compound addition.

FIG. 11 is the different kinetics of the mass redistribution due to agonist-induced GPCR activation.

FIG. 12 is the compound-dependant total responses of agonist-induced mass changes in the Stage 3 as highlighted in FIG. 2.

FIG. 13 is a time-dependent LID response of Chinese Hamster Ovary (CHO) cells before and after compound addition. The compound concentration used is 10 µM for all compounds.

FIG. 14 a time-dependent LID response of engineered Chinese Hamster Ovary (CHO) cells with over-expressed rat muscarnic receptor subtype 1 (thus this cell line is termed as M1 CHO) before and after compound addition. The compound concentration used is 10 µM for all compounds.

FIG. 15 compares the compound-dependant total responses in the Stage 3 as highlighted in FIG. 2 for two distinct cell lines.

FIG. 16 is a time-dependent LID response of two types of cells (CHO and M1 CHO) before and after addition of oxotremorine M (10 µM). Before the compound addition, the cells are pre-incubated either HBSS buffer (Invitrogen) (referred to "without DIP") or with dynamin inhibitory peptide (DIP) at a concentration of 50 µM for 45 minutes.

FIG. 17 is a time-dependent LID response of two types of cells (CHO and M1 CHO) before and after addition of clonidine (10 µM). Before the compound addition, the cells are pre-incubated either HBSS buffer (Invitrogen) (referred to "without DIP") or with dynamin inhibitory peptide (DIP) at a concentration of 50 µM for 45 minutes.

DETAILED DESCRIPTION OF THE DRAWINGS

Figure 1:
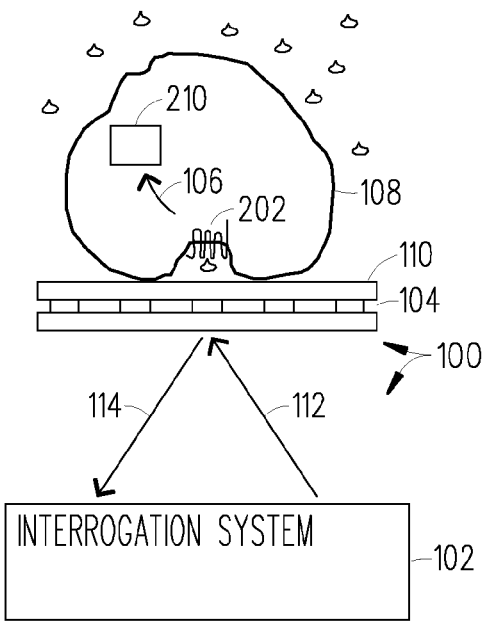
FIG. 1 is a diagram showing an optical LID system being used to monitor a mass redistribution (e.g. GPCR translocation) within a living cell in accordance with the present invention.

Referring to FIG. 1, there is a diagram that shows the basic components of an optical LID system 100 which includes an interrogation system 102 and an optical LID biosensor 104 that are used to detect and monitor a mass redistribution (e.g., the translocation of a GPCR 202, as seen in the arrow numbered 106) within a living cell 108 (only one shown) located on a surface 110 of the optical LID biosensor 104. In the preferred embodiment, the interrogation system 102 interrogates the optical LID biosensor 104 (e.g., SPR sensor 104, waveguide grating sensor 104) so it can detect and monitor the mass redistribution within the living cell 108. This is done by emitting an optical beam 112 which has the appropriate spectral or angular content towards the optical LID biosensor 104 such that when the optical beam 112 is reflected by the sensing surface 110, the resonant angle or wavelength response which identifies the mass redistribution becomes dominant in the reflected beam 114. Thus, when there is a detectable mass redistribution within the living cell 108, the optical LID biosensor 104 can sense a response change which is observed as an angular or wavelength change in the reflected beam 114. The optical response may be recorded as a function of time. In this way, the kinetics of any event that leads to a mass redistribution within the living cell 108 can be analyzed. Prior to discussing several different types of living cell-based assays that can be conducted and monitored by the optical LID system 100 (see FIGS. 2-18) a detailed discussion is provided about some of the various components within the living cell 108.

Due to the limited range (~hundreds nanometers) of the electromagnetic field propagating in the optical LID sensor 104 that can extend into the surrounding media (e.g, adherent cell 108) as an evanescent electromagnetic field (the depth is referred to the penetration depth or sensing volume), only the mass redistribution 106 in the lower portion of the adherent cells that is close to the sensor surface 110 can be detected. Biological cells 108 are complex structures with components ranging in size from nanometers to tens of microns. The cell 108 has a cytoplasm (10-30 μM) that contains numerous organelles. The largest organelle is the nucleus, whose size ranges between 3 and 10 μm. The nucleus is filled with DNA-protein complexes and proteins, the most important one being chromatin. Mitochondria are small organelles comprised of a series of folded membranes with sizes ranging from 0.5-1.5 μm. Other cell components include endoplasmic reticulum (ER) (0.2-1 μm), lysomes (0.2-0.5 μm), peroxisomes (0.2-0.5 μm), endosomes (~100 nm), and gogli. Living cells 108 are highly dynamic and most organelles travel extensively within cells. For example, microtubules can transport organelles over long distances. A stimulus can result in the submicron movement of densely packed organelles in the very periphery of a sensor surface 100 on which the cells 108 are cultured; such movement leads to mass redistribution 106 within the cell 108. The mass redistribution 106 can be detected by an optical biosensor 104; the signal relating to mass redistribution 106 is referred to as directional mass redistribution (DMR) signal.

Cellular trafficking could occur if secretory organelles are to occupy their docking site beneath the plasma membrane, and if endocytic vesicles at the plasma membrane are to reach their processing stations in the cytosol. In either direction, organelles must penetrate the so-called actin cortex beneath the plasma membrane, a dense meshwork of actin filaments that is up to a few hundred nanometers thick. To the extent that actin filaments constantly assemble and disassemble, the meshwork is dynamic and permeable to organelles. Control mechanisms regulating the assembly and disassembly would also regulate the permeability of the actin cortex.

The plasma membrane is a busy place. Exocytic vesicles insert receptors into the plasma membrane and release ligands into the extracellular space. Endocytic vesicles carry receptors with bound ligand to internal processing stations. Caveolae are plasma-membrane-associated vesicles with a presumed role in cell signaling. Lipid rafts are thought to populate the plasma membrane as small floating islands in which select membrane proteins meet in private to exchange signals. Finally, there is the universe of membrane receptors. Many are probably embedded in large molecular complexes that continually recruit and release downstream effector molecules.

Transport of cellular components or extracellular stimuli not only occurs at the plasma membrane, but also occurs at multiple intracellular compartments. These events include (1) protein target or substrate recruitment to the nucleus, to the membrane, to the cytosol, throughout recycling pathways, to or from other organelles, uptake from extracellular space (ligand binding, gene transfection, infection and protein delivery); (2) redistribution of newly synthesized intracellular components within various functional compartments at defined microenvironments and with mediated release locations. These cellular events lead to directional mass redistributions at certain times during signaling cycles.

From hereinafter, several different types of living cell-based assays that can be conducted and monitored by the optical LID system 100 are described in detail below with respect to FIGS. 2-18.

Figure 2:
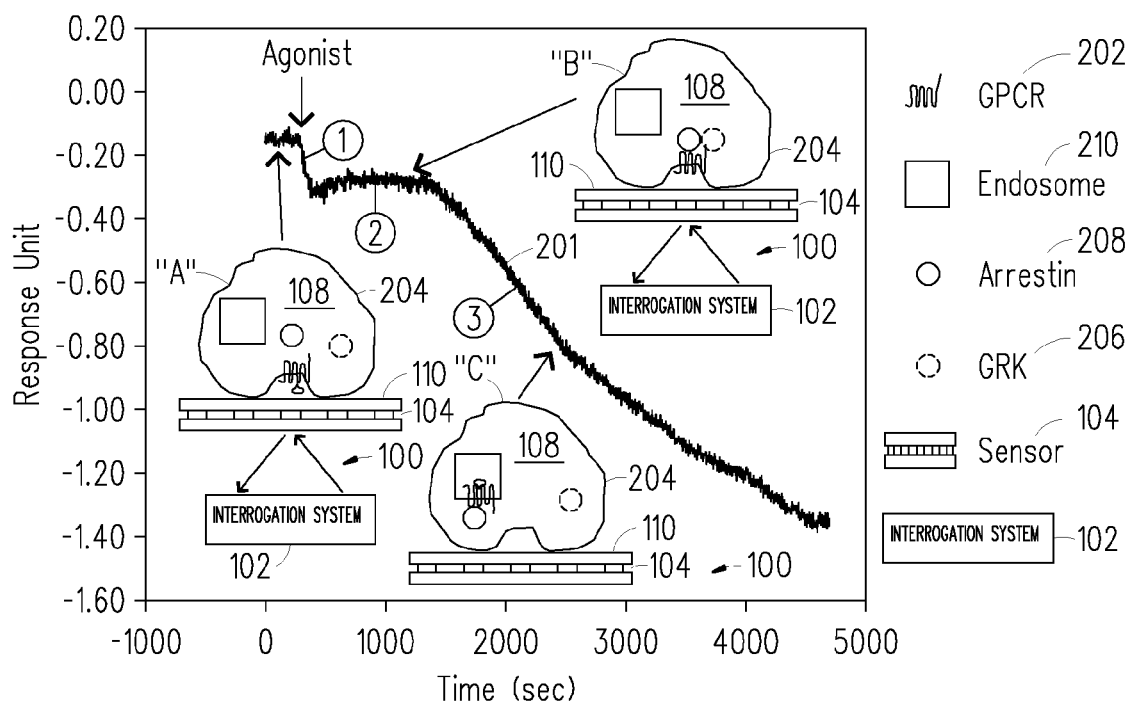
FIG. 2 is a diagram that shows the different states associated with the GPCR translocation within the living cell that can be identified by analyzing the time dependent optical response output from the optical LID system shown in FIG. 1 in accordance with the present invention.

Referring to FIG. 2, there is shown a diagram where the optical LID system 100 is used to monitor an agonist-induced translocation of G protein coupled receptors 202 (GPCRs 202) within a living cell 108 (only one shown) located on the top surface 110 of the optical LID biosensor 104. In particular, the diagram illustrates an agonist induced and time-dependent optical response 201 that partly is due to the translocation of a target GPCR 202 within the living cell 108. The cell is adherent on the top surface 110 of the waveguide-based biosensor 104. For clarity, the interrogation system 102 is not shown in the portion labeled as "C".

As can be seen, the GPCR 202 in the resting state resides at the cell surface 204 (plasma membrane 204), while the GPCR kinase 206 (GRK 206) and arrestin 208 are uniformly distributed inside the living cell 108 (see diagram "A"). Upon agonist activation, the GPCR 202 activates heterotrimeric G proteins composed of $\alpha$, $\beta$, and $\gamma$ subunits. The G$\alpha$ and G$\beta\gamma$ subunits dissociate which causes the GRK 206 to be recruited to the receptor 202 at the plasma membrane 204. Then, the GRK 206 phosphorylates the carboxy terminus of the GPCR 202. And, β-arrestin 208, a relatively abundant intracellular protein, rapidly (within minutes) translocates within the cytoplasm to the activated GPCR 202 at the plasma membrane 204, binds the GRK-phosphorylated receptor, and uncouples the receptor from its cognate G protein. The β-arrestin 208 then binds to the desensitized GPCR 202 and translocates to clathrin-coated pits at the cell surface 204 where the receptor 202 is internalized in clathrin-coated vesicles (CCV) (see diagram "B"). Finally, the entire complex 202 and 206 is delivered to the endosome 210 (endocytic vesicle 210) (see diagram "C"). This process is known as translocation. For more information about GPCR translocation, reference is made to the following three articles:

Drews, J. "Drug discovery: a historical perspective." Science 2000, 287, 1960-1963;
Ma, P. and Zemmel, R. "Value of novelty". Nat. Rev. Drug Discov. 2002, 1, 571-572.
Pierce, K. L. et al. "Seven-transmembrane receptors." Nat. Rev. Mol. Cell Biol. 2002, 3, 639-650.

The contents of these documents are incorporated by reference herein.

It should be appreciated that these translocation events lead to directional mass distribution (e.g., towards the cell surface or leaving the cell surface) within the living cells 108 at a certain time, therefore resulting in different optical responses through a prolong period of time. Another possible biological event that can lead to directional mass distribution is the cell morphological changes due to the GPCR activation. The cell morphological changes involve the cytoskeleton rearrangement as well as cell adhesion changes. Cytoskeleton is a complex network of protein filaments that extends throughout the cytoplasm of eucaryotic cells and is involved in executing diverse activities in these cells. As well as providing tensile strength for the cells it also enables muscle contraction, carries out cellular movements and is involved in intracellular signaling and trafficking, cell division and changes in the shape of a cell. Activation of G-protein coupled receptors (GPCR) leads to at least two independent events that theoretically could exert an effect on the cytoskeleton rearrangement. The first event is the activation of the intracellular signaling pathway, and the second is a receptor-mediated endocytosis (i.e., translocation), which occurs after an agonist activation of the majority of GPCR. Activation of an intracellular signaling pathway after an agonist/GPCR binding then leads to two further sets of connected events. Processes in the first set lead to the activation of a secondary intracellular signaling pathway (G protein→effector→message), while the mechanisms of the second set regulate the degree of signaling within the cell by affecting the events in the first set. These mechanisms include phosphorylation/desensitization, internalization and downregulation of membrane-bound receptors. It is assumed that both sets of events can lead to the rearrangement of actin filaments within the cell. For example, after the activation of GPCR, various forms of G proteins (e.g. $G_\alpha$ and $G_{\beta\gamma}$) can bind with F-actin filaments; and those and other signaling molecules can disassociate from actin filaments. The internalization process of membrane-bound receptors that occurs via receptor-mediated endocytosis could also be responsible for the dynamics of actin filaments.

Referring again to FIG. 2 and in accordance with the present invention, the different states associated with GPCR translocation within a living cell 108 can be identified and monitored by analyzing the optical response 201 from the optical LID system 100. In fact, three different events can be identified when looking at the optical response 201 shown in FIG. 2. The three major events that can be seen include: (1) a very large and sharp decrease in signal 201 upon the addition of agonist, due to bulk index of refraction changes (i.e., generally the compound solution has relatively lower refractive index than the cell medium. Thus compound addition results in a decreased LID signal); (2) a transition stage which has slow changes in the response signal 201 and lasts almost 20 minutes: this stage might be related to the phosphorylation of the activated receptors 202 by GRKs 206, arrestin binding, desensitization of the receptors 202 to chathrin-coated pits, and/or other cellular responses; and (3) a slow decrease of response signal 201 which lasts almost 50 minutes, corresponding to the translocation of the GPCR complexes 202 and 208 to the endosome 202. In other cases, an additional event that immediately followed the initial step can be evident (e.g., FIG. 11); that is an increase of response signal 201, mainly due to diffusion of the compound in the cell medium and/or recruitment of intracellular components to activated GPCRs at cell surface. Details about how this test can be performed by the optical LID system 100 are described below with respect to method 300 shown in FIG. 3.

Figure 3:
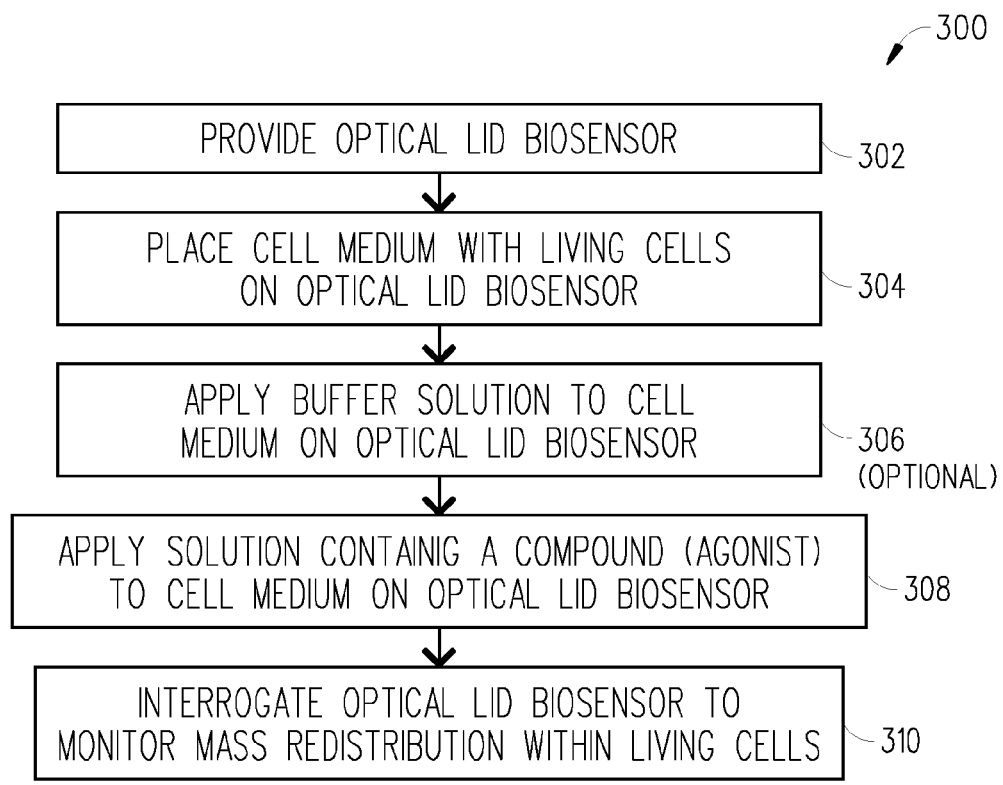
FIG. 3 is a flowchart illustrating the basic steps of a method for monitoring in real time an agonist-induced mass redistribution including GPCR translocation within living cells using an optical LID biosensor in accordance with the present invention.

Referring to FIG. 3, there is shown a flowchart illustrating the basic steps of a method 300 for monitoring in real time the mass redistribution due to an agonist-induced GPCR activation within living cells 108 using an optical LID biosensor 104 in accordance with the present invention. The method 300 includes the following steps: (a) provide an optical LID biosensor 104 (step 302); (b) place a certain number of living cells 108 in a medium which covers the optical LID biosensor 104 such that the living cells 108 attach onto the surface 110 of the optical LID biosensor 104 (step 304); (c) optionally apply a buffer solution at least once into the cell medium (step 306); (d) apply a solution containing a compound (agonist) into the cell medium (step 308); and (e) interrogate the optical LID biosensor 104 and monitor the time dependent optical response 201 of the living cells 108 cultured on the optical LID biosensor 104 (step 310).

It should be appreciated that if step 306 is performed and a buffer solution (the same buffer solution that is used to formulate the compound of interest) is applied to the living cells 108 before applying the compound, any unwanted effect, due to the living cells 108 responding to the environmental changes, can be minimized. This is possible because living cells 108 that are cultured on the optical. LID biosensor 104 are alive and dynamic which means that they can sense changes in the surrounding medium compositions as well as temperature and can respond to those changes. However, as the living cells 108 senses changes like the addition of a buffer then they tend to become resistant to those changes in the medium composition assuming no additional chemical is introduced.

It should also be appreciated that the real time method 300 provides quantifiable information, and equally important, it provides the kinetics of the mass redistribution within cells due to GPCR activation. In contrast to traditional methods of screening GPCRs, this method 300 is simpler to perform, more sensitive, label-independent and is applicable to all GPCRs 202 without requiring prior knowledge of natural ligands or how a given receptor is coupled to downstream signaling pathways.

It should also be appreciated that in the step 304 the number of cells should be optimized such that after a certain time cultured under optimal conditions the cells become adherent and reach high confluency (optionally larger than 75%) on the surface 110 of optical LID sensor 104 in order to achieve high sensitivity.

Figure 4:
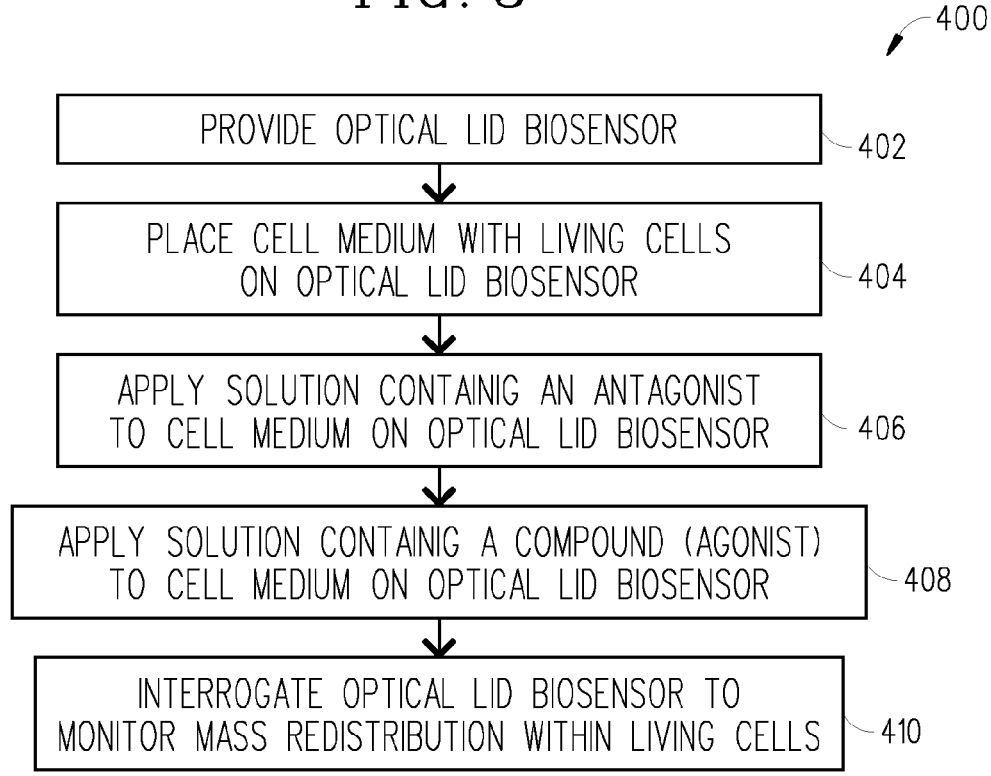
FIG. 4 is a flowchart illustrating the basic steps of a method for screening an agonist against a target GPCR based on mass redistribution within living cells using the optical LID biosensor in accordance with the present invention.

Referring to FIG. 4, there is shown a flowchart illustrating the basic steps of a method 400 for screening an agonist against a target GPCR 202 based on mass redistribution within living cells 108 using the optical LID biosensor 104 in accordance with the present invention. The method 400 includes the following steps: (a) provide the optical LID biosensor 104 (step 402 step 510); (b) place a certain number of living cells 108 in a medium which covers the optical LID biosensor 104 such that the living cells 108 attach onto the surface 110 of the biosensor 104 (step 404); (c) apply a solution containing an antagonist with a known affinity at a certain concentration into the cell medium for a certain time until the optical LID biosensor 104 becomes stabilized (step 406); (d) apply a solution containing a compound (agonist) into the cell medium (step 408) where the concentration of the compound is sufficiently high to compete off the receptor-bound antagonist; and (e) interrogate the optical LID biosensor 104 and monitor the time dependent optical response 201 of the living cells 108 cultured on the optical LID biosensor 104 (step 410).

It should be appreciated that in this method 400 by pre-applying the antagonist to one receptor in the living cells 108, effectively enables one to screen the compounds for their agonism against this particular receptor. Moreover, it should be appreciated that this method 400 is similar to the previous method 300 except for one difference in that method 400 requires pre-knowledge about the functionality of the compound for its cognate receptor in the living cells 108. For instance, one needs to know whether the antagonist inhibits the activation of GPCR 202, or whether the antagonist activates the GPCR 200 which leads to translocation.

Figure 5:
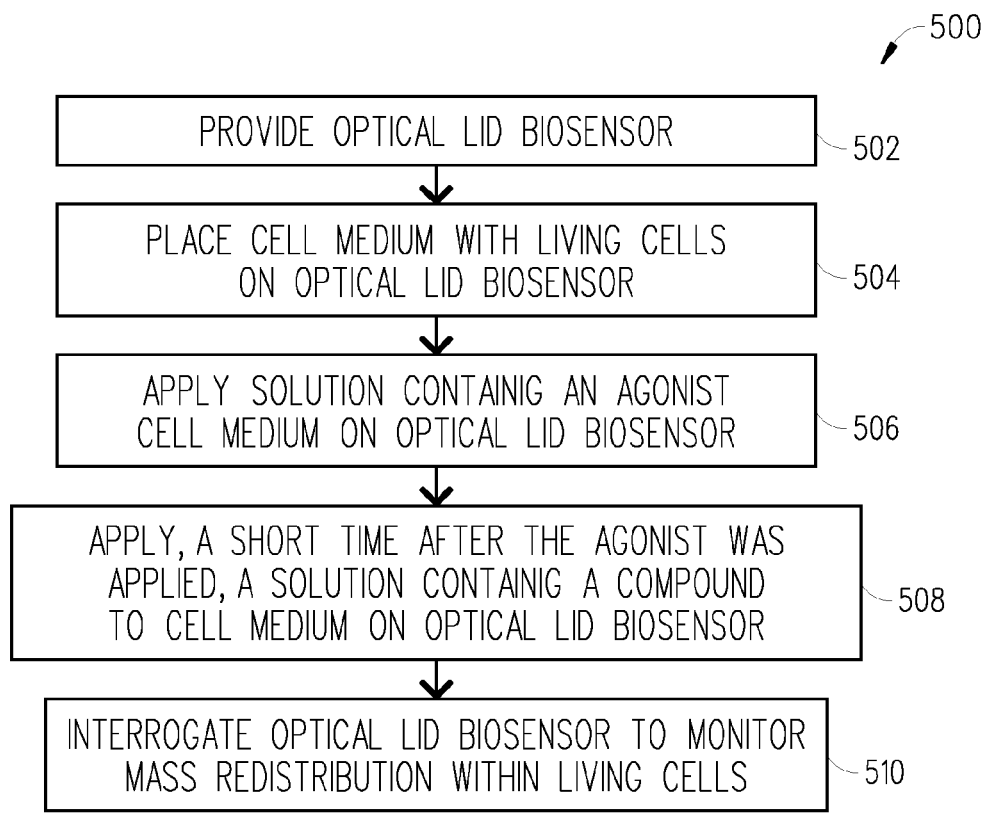
FIG. 5 is a flowchart illustrating the basic steps of a method for screening an antagonist against a target GPCR based on mass redistribution within living cells using the optical LID biosensor in accordance with the present invention.

Referring to FIG. 5, there is shown a flowchart illustrating the basic steps of a method 500 for screening an antagonist against a target GPCR 202 based on mass redistribution within living cells 108 using the optical LID biosensor 104 in accordance with the present invention. The method 500 includes the following steps: (a) provide an optical LID biosensor 104 (step 502); (b) place a certain number of living cells 108 in a medium which covers the optical LID biosensor 104 such that the living cells 108 attach onto the surface 110 of the biosensor 104 (step 504); (c) apply a solution containing an agonist which has a known affinity at a certain concentration into the cell medium for a short time such that the translocation does not happen (step 506); (d) after this short time, apply a solution containing a compound having a certain concentration into the cell medium (step 508); and (e) interrogate the optical LID biosensor 104 and monitor the time dependent optical response 201 of the living cells 108 cultured on the optical LID biosensor 104. It should be appreciated that like method 400, this method 500 requires pre-knowledge about the target GPCR 202 in the living cells 108 and also requires the pre-selection of an antagonist or agonist for pre-treating the living cell 108 against this particular GPCR 202.

It should be appreciated that the step 506 and the step 508 can be combined into one step; that is, the agonist known to the target GPCR in the cell can be added into together with a compound. It also should be appreciated that similar to the method 300, the compound to be tested can be introduced first, followed by the addition of the known of agonist.

Each of the methods 300, 400 and 500 can be further enhanced by using a self-referencing optical LID biosensor 104. It is well known that the performance of the optical LID biosensor 104 is generally affected by the designs and characteristics of the sensor, the optics, and by the environmental fluctuations including ambient temperature and pressure. A main advantage of using the self-referencing optical LID biosensor 104 is that the top surface 110 has both a reference region and a sample region which enables one to use the sample region to detect the mass redistribution in the living cells 108 and at the same time use the reference region which does not have living cells 108 attached thereto to reference out spurious changes that can adversely affect the detection of the mass redistribution within the living cells 108.

Figure 6:
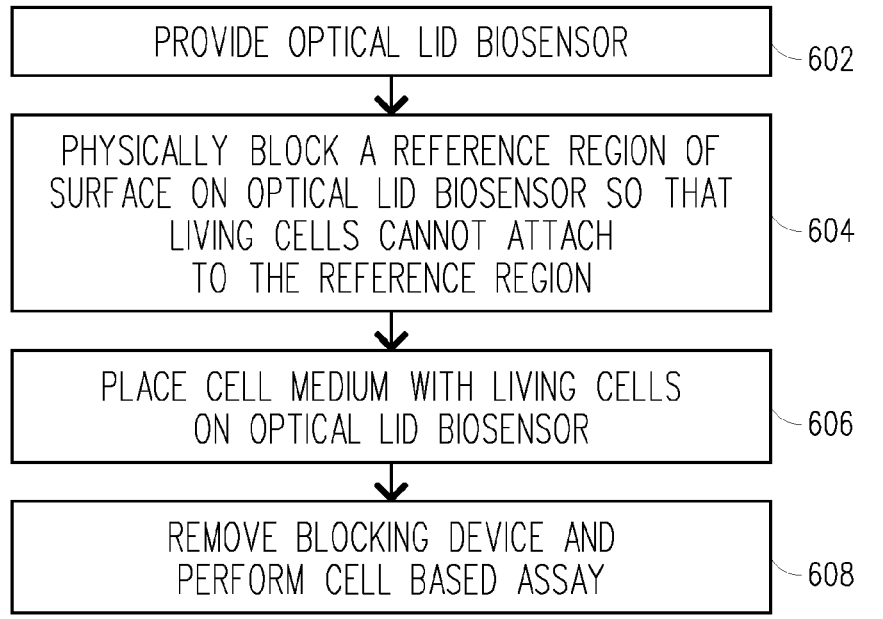
FIG. 6 is a flowchart illustrating the basic steps of a method for creating a self-referencing optical LID biosensor that can be used in any one of the methods shown in FIGS. 3-5 in accordance with the present invention.

In one embodiment, the self-referencing optical LID biosensor 104 can be made in accordance with method 600 shown in FIG. 6. This self-referencing optical LID biosensor 104 can be created by using the following steps: (a) provide the optical LID biosensor 104 (step 602); (b) physically block one region (reference region) of the surface 110 of the optical LID biosensor 104 by using a soft stamp (e.g., rubber stamp) (step 604); (c) place a certain number of living cells in a growth medium which covers an unblocked region (sample region) of the optical LID biosensor 104 (step 606); and (d) remove the soft stamp after the living cells 108 have attached to the unblocked region on the optical LID biosensor 104 (step 608). At this point, the living cell-based assay can be performed as described in methods 300, 400 and 500. It should be appreciated that different methods can also be applied to create the self-referencing LID sensors for cell studies. For example, a physical barrier can be used to divide the sensor into two portions, and cells in a medium are only applied to cover one portion. After cell adhesion, the physical barrier can be removed.

Referring now to another feature of the present invention, it is well known that multiplexed cell assays have become increasingly important, not only for increasing throughput, but also for the rich and confirmative information available from a single assay. As such, it is desirable if the present invention could be further enhanced to perform multiple living cell-based assays at the same time.

Figure 7:
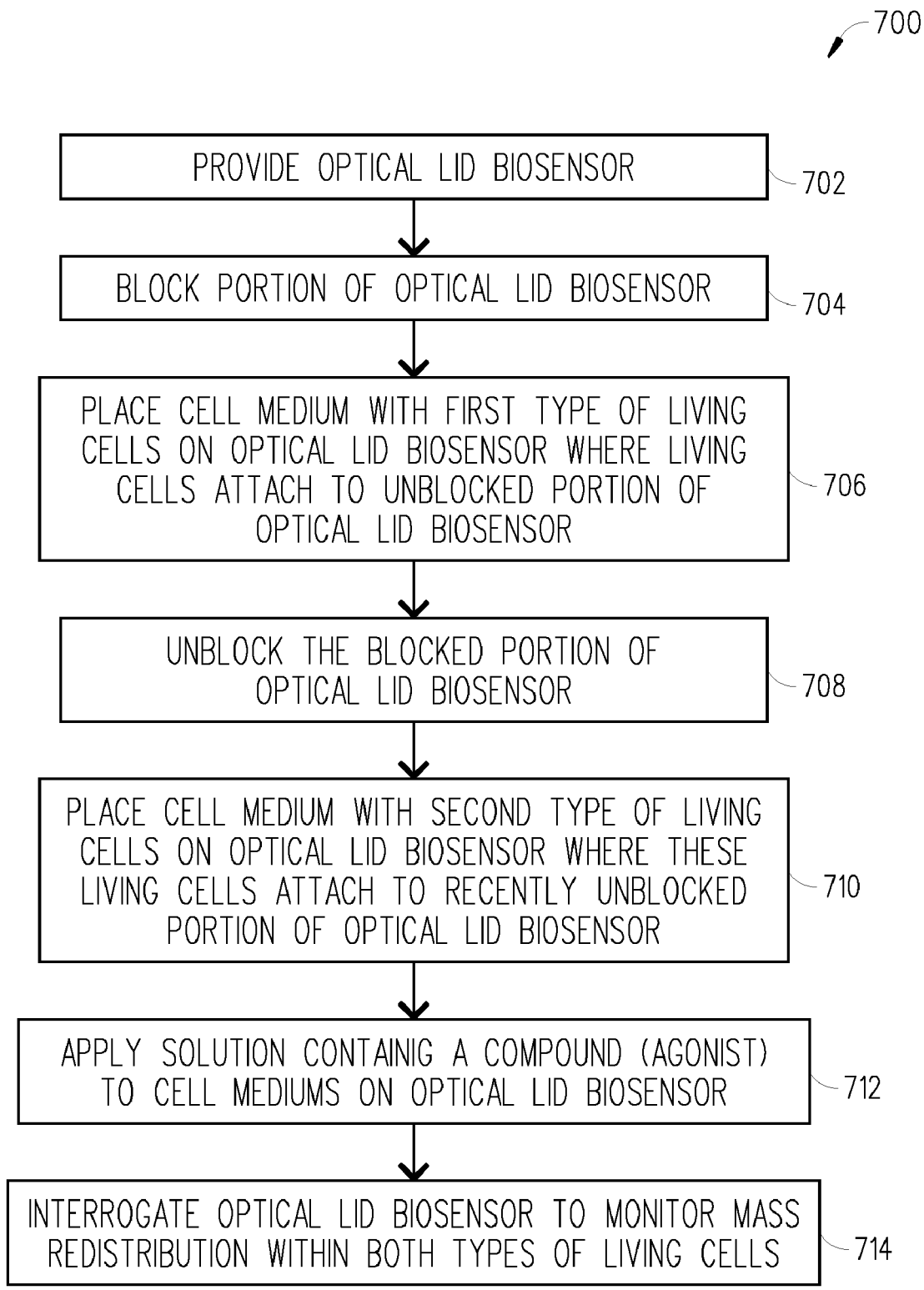
FIG. 7 is a flowchart illustrating the basic steps of another method for creating a self-referencing optical LID biosensor that hosts two types of cells adherent at spatially separated regions within the same sensor and can be used in any one of the methods shown in FIGS. 3-5 in accordance with the present invention.

In one embodiment, the present invention can be enhanced to perform multiple living cell-based assays at the same time by using the method 700 shown in FIG. 7. In accordance with method 700 one can monitor mass redistribution due to agonist-induced GPCR activation within multiple types of the living cells 108 by: (a) providing an optical LID biosensor 104 (step 702); (b) blocking a portion of the top surface 110 of the optical LID biosensor 104 by using a stamp that prevents the attachment of the living cells 108 to that portion of the optical LID biosensor 104 (step 704); (c) placing a first type of living cells 108 in a cell medium which covers the unblocked portion of the surface 110 of the optical LID biosensor 104 so the living cells 108 are able to attach to the unblock portion of the surface 110 of the optical LID biosensor 104 (step 706); (d) removing the stamp from the top surface 110 of the optical LID biosensor 104 (step 708); (e) placing a second type of living cells 108 in a cell medium which covers the optical LID biosensor 104 so the second type of living cells 108 are able to attach to the recently uncovered top surface 110 of the optical LID biosensor 104 (step 710); (f) applying a solution containing a compound into the cell medium located on the top surface 110 of the optical LID biosensor 104 (step 712); and (g) interrogating the optical LID biosensor 104 to monitor time dependent optical responses 201 which indicate mass redistributions within the two types of living cells 108 on the optical LID biosensors 104 (step 714).

It should be appreciated that the two types of cells can be related; e.g., Chinese Hamster Ovary (CHO) cells versus engineered CHO cells containing an overexpressed target receptor. This approach not only enables multiplexed cell assays, but also provide confirmative results regarding to the compound effect on the target receptor by comparison of the optical responses of the same compound acting on two different cells, since two cells are identical except for the target receptor expression level.

Figure 8:
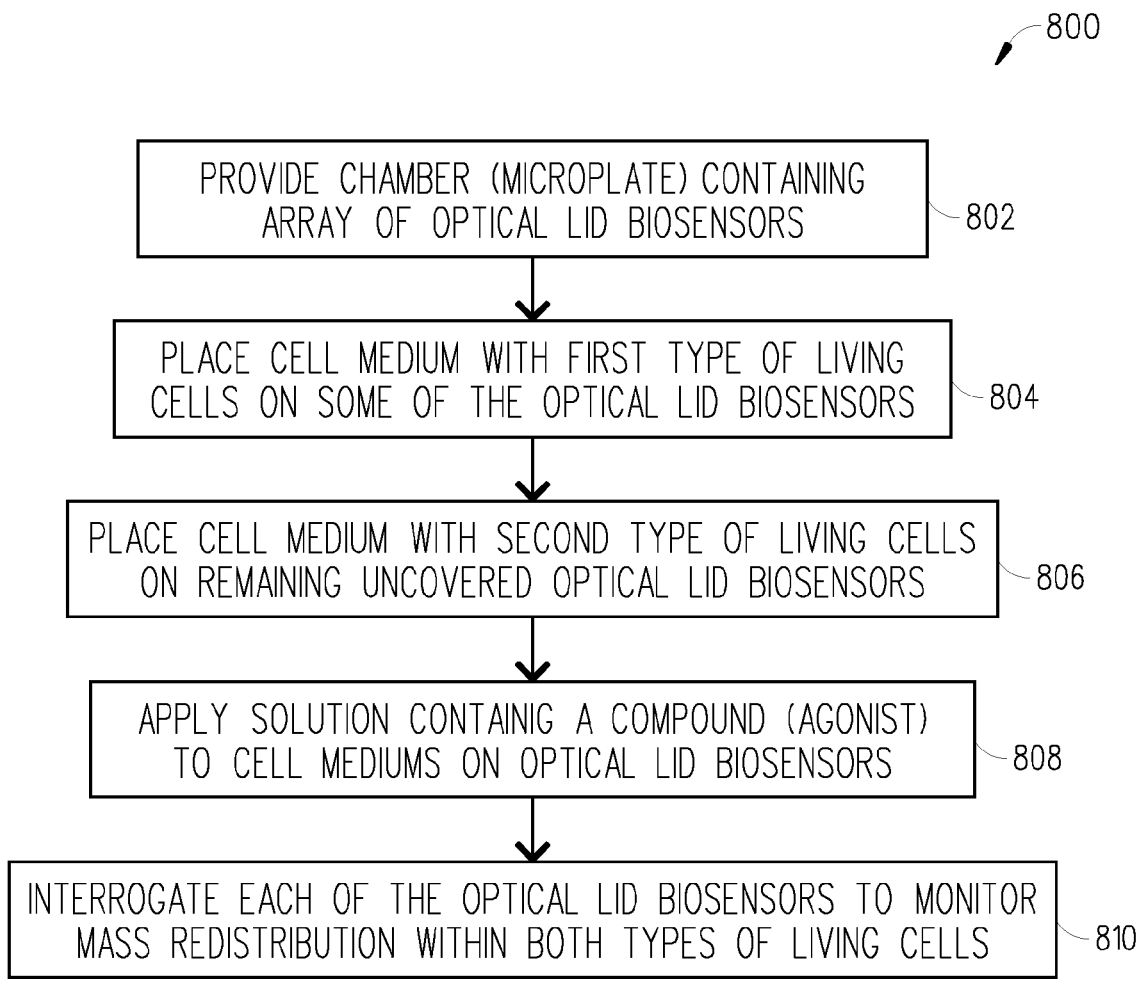
FIG. 8 is a flowchart illustrating the basic steps of a method for monitoring an agonist-induced GPCR mass redistribution within multiple types of living cells using the optical LID biosensor in accordance with the present invention.

In another embodiment, the present invention can be enhanced to perform multiple living cell-based assays at the same time using the method 800 shown in FIG. 8. In accordance with method 800 one can monitor the mass redistribution due to agonist-induced GPCR activation in multiple types of living cells 108 by: (a) providing a chamber (microplate) containing an array of the optical LID biosensors 104 (step 802); (b) placing a first type of living cells 108 in a cell medium which covers one or more of the optical LID biosensors 104 so the first type of living cells 108 are able to attach to the surfaces 110 of the one or more optical LID biosensors 104 (step 804); (c) placing a second type of living cells 108 in a cell medium which covers one or more of the remaining uncovered optical LID biosensors so the second type of living cells 108 are able to attach to the surfaces 110 of the one or more remaining uncovered optical LID biosensors 104 (step 806); (d) applying a solution containing a compound into the cell mediums located on the top surfaces 110 of covered optical LID biosensors 104 (step 808); and (e) interrogating the covered optical LID biosensors 110 to monitor the time dependent optical responses 201 which indicate mass redistributions within the living cells 108 on each of the covered optical LID biosensors 104 (step 810).

It should be appreciated that arrays of different DNA vectors containing distinct target receptor genes in combination with transfection reagents can be deposited onto a LID sensor; a single type of cells is placed and overlaid with such array and uptakes the genes. Thus only cells overlaid on each spot area become transfected and therefore forming a transfected cell cluster array (U.S. Pat. No. 6,544,790 B1 "Reverse transfection method"). Similarly, array of functional receptor proteins in complexed with protein delivery reagents can be used to similar transfected cell cluster array (US2004/0023391A1 "Methods and devices for protein delivery"). Both types of transfected cell arrays can be used for compound screening using the current technology.

Figure 9:
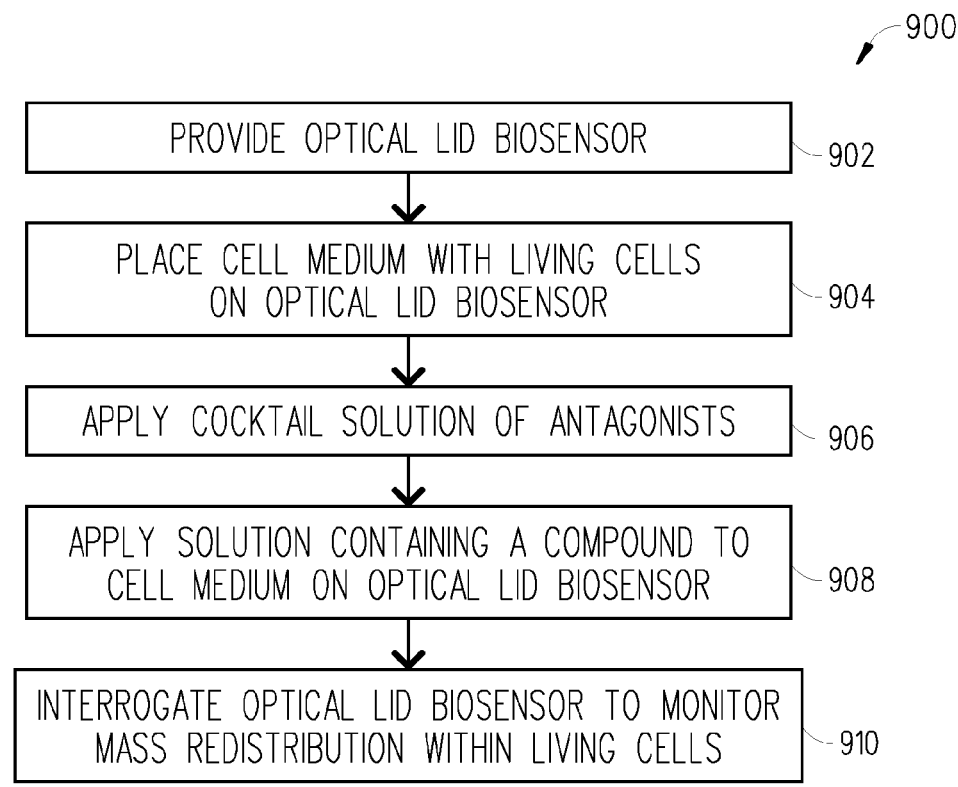
FIG. 9 is a flowchart illustrating the basic steps of a method for screening agonists against multiple GPCRs within a single type of living cell based on mass redistribution using the optical LID biosensor in accordance with the present invention.

In yet another embodiment, the present invention can be further enhanced to perform multiple target screens in a single type of cells at the same time by using method 900 shown in FIG. 9. In accordance with method 900 one can screen agonists against multiple GPCRs 202 within a single type of living cells 108 by performing the following steps: (a) providing a optical LID biosensor 104 (step 902); (b) placing the living cells 108 in a cell medium which covers the optical LID biosensor 104 so the living cells 108 are able to attach to the surface 110 of the optical LID biosensor 104 (step 904); (c) applying a solution containing a cocktail solution of antagonists (step 906); (d) applying a solution containing a compound into the cell medium located on the top surface 110 of the optical LID biosensor 104 (step 908); and (e) interrogating the optical LID biosensor 104 to monitor a time dependent optical response 201 which indicates mass redistributions within the living cells 108 (step 910).

It should be appreciated that similar method can be used to screen antagonist against multiple receptors in the same cell line by modifying the method 900. Instead of a cocktail solution of antagonists in the step 906, one can use a solution of compounds of interest; at the same time, a cocktail solution of agonists is used to replace the compound solution in the step 908.

Following is a discussion about the results of several different experiments that were conducted to show that an optical LID system 100 can be used to monitor a mass redistribution within living cells 108 that are located on the surface 110 of the optical LID biosensor 104 (see FIG. 2).

Figure 10:
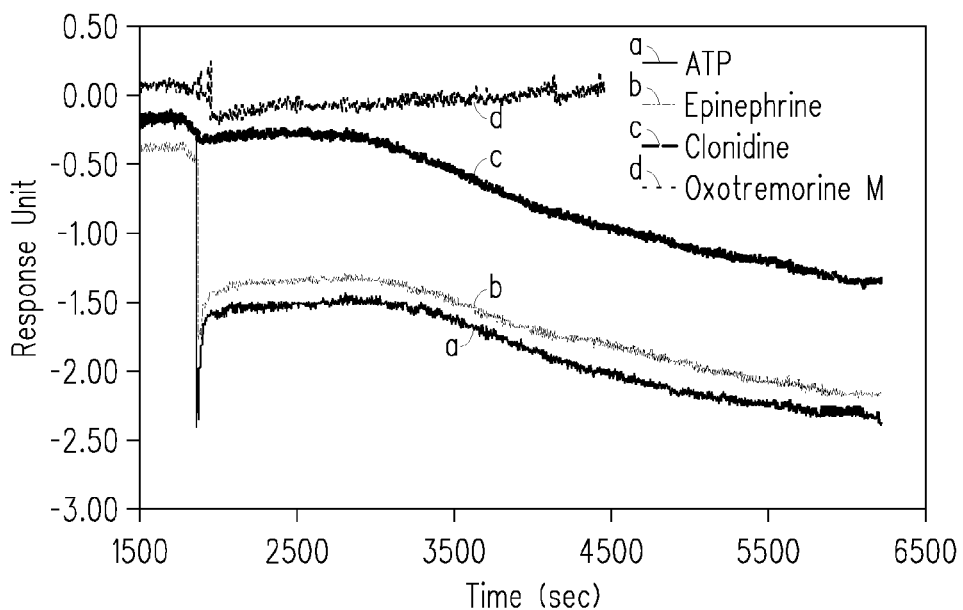
FIGS. 10-17 are various graphs and charts indicating the results of several different experiments that were conducted to show that the optical LID system can be used to monitor mass redistributions like GPCR translocations within living cells that are located on a surface of the optical LID biosensor in accordance with the present invention. This data was obtained using an optical waveguide grating sensor system and LID microplates ($Nb_2O_5$ plates), manufactured by Corning Incorporated.

FIG. 10 is a graph that shows several agonist-induced responses within chinese hamster ovary cells 108 (CHO 108) that were monitored by the optical LID system 100. It is known that CHO cells 108 endogenously express beta adrenergic receptors, alpha2-adrenergic receptors, P2Y receptors, as well as beta-arrestin and GRKs. It is also known that muscarinic receptors are endogenously expressed at very low level in the CHO cells 108. In this experiment, approximately $\sim 5 \times 10^4$ CHO cells 108 were placed within each well of a microplate that contained an array of optical LID biosensors 104. The CHO cells 108 were then cultured in 150 µl serum medium for 24 hours to ensure that the CHO cells 108 became adherent to the substrate surface 110.

The graph shows the optical responses of the CHO cells 108 to four different compounds which were examined: (1) ATP (100 µM), agonist for P2Y receptors; (2) clonidine (10 µM), agonist for alpha2-adrenergic receptors; (3) epinephrine (100 µM), agonist for beta adrenergic receptors; and (4) oxotremorine M (10 µM), agonist for muscarinic receptors. Since muscarinic receptors are endogenously expressed at very low level in CHO cells 108; oxotremorine M, agonist for muscarinic receptors, served as a control. Each of these agonists was directly applied to a different one of the wells which contained the serum medium. The optical responses were then collected by the optical LID system 100.

Figure 11:
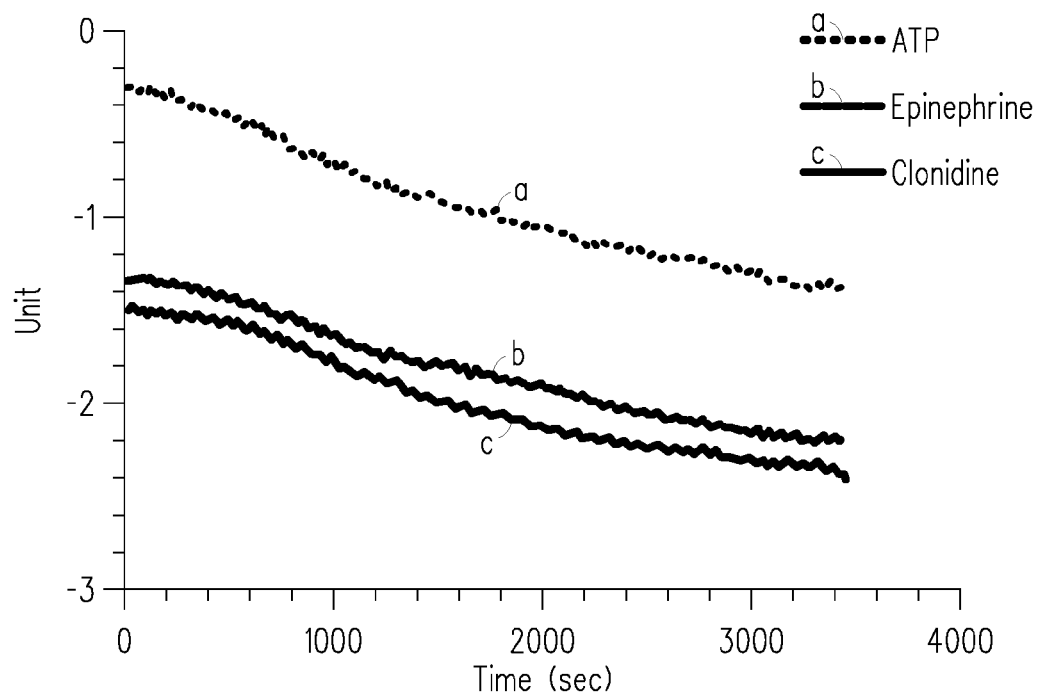
Figure 12:
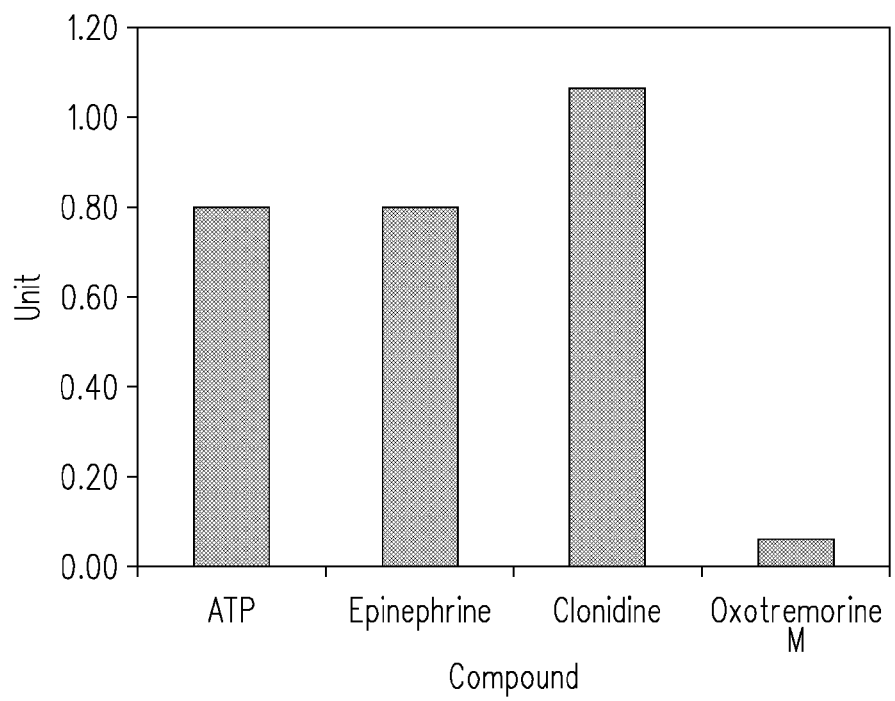

The results showed that these adherent CHO cells 108 gave rise to similar kinetics and transitions as shown by the optical responses after the introduction of the three agonists: ATP, clonidine, and epinephrine. Oxotremorine M caused almost no cell response. In FIG. 11, a kinetics analysis of the later stage of the process revealed that all three agonists (ATP, epinephrine, clonidine) resulted in a similar slow process. The changes for the Stage 3 as shown in FIG. 2, caused by those agonists, are shown in the graph in FIG. 12. The similar changes might reflect the fact that beta-arrestin, a critical component for GPCR translocation, could be the limiting factor in the CHO cells 108, given that the size of clathrin-coated pits and beta-arrestin are similar.

Figure 13:
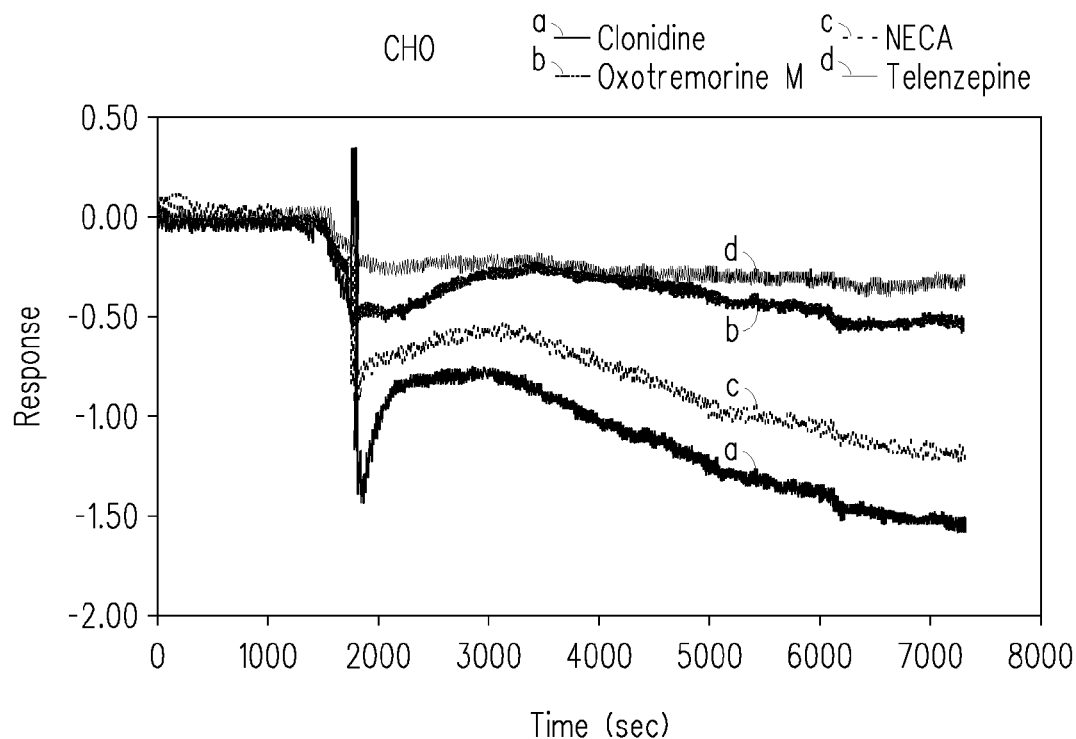

FIG. 13 is a graph that shows the results from an experiment which indicates the ligand- and time-dependent response of a monolayer of living CHO cells 108 on wave-guide biosensors 104. The agonists which were used included: (1) clonidine; (2) oxotremorine M; (3) NECA; and an telenzepine, an antagonist for M1 receptor, is also used.

Figure 14:
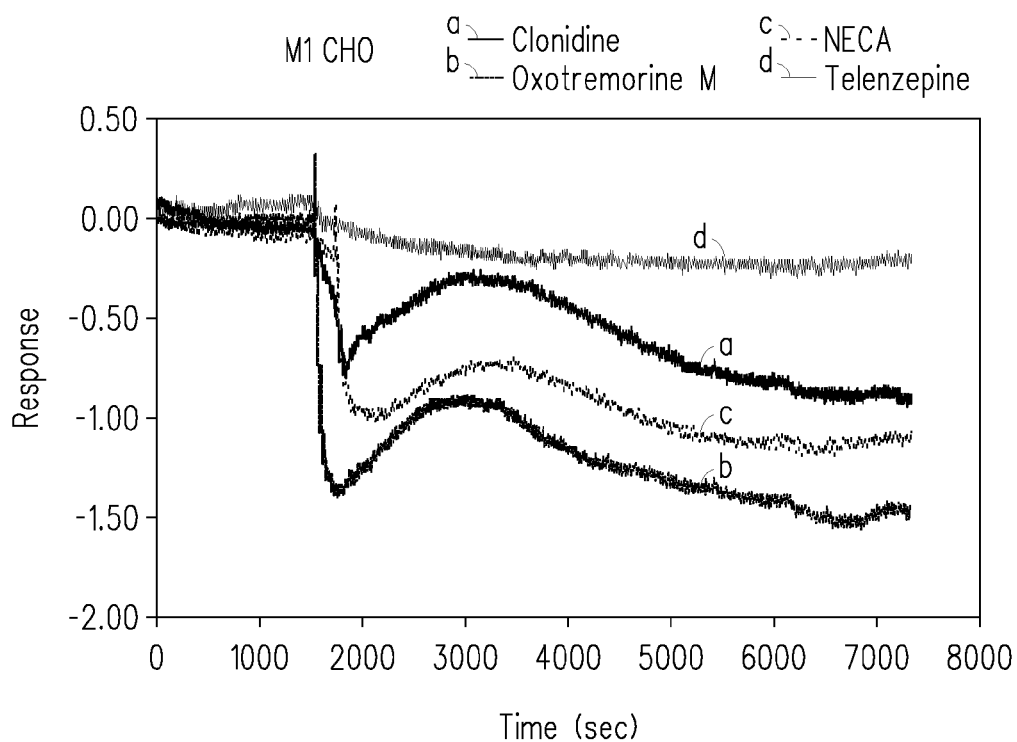

FIG. 14 is a graph that shows the results from an experiment which indicates the ligand- and time-dependent response of monolayer of living CHO cells 108 with stably overexpressed rat muscarinic receptor subtype 1 (M1) on wave-guide biosensors 104. The agonists which were used included: (1) clonidine; (2) oxotremorine M; and (3) NECA; and an telenzepine, an antagonist for M1 receptor, is also used.

Figure 15:
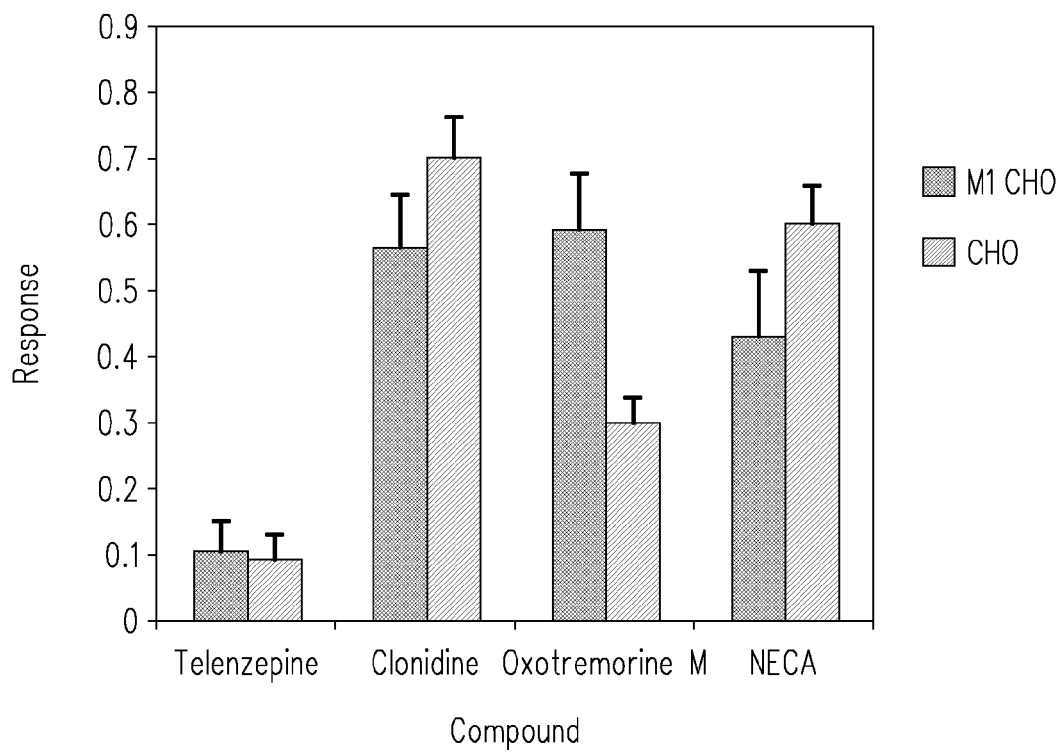

FIG. 15 is a graph that shows the results from an experiment which indicates the ligand-induced total change in response of monolayer of living CHO cells 108 without (CHO) and with stably overexpressed rat muscarinic receptor subtype 1 (M1CHO) on wave-guide biosensors 104. Results shown in FIGS. 11 and 13-15 indicated that (1) there are alpha2 adrenergic receptors expressed in both CHO and M1-CHO cells; and their agonist (clonidine) induced mass redistribution signals; (2) there is relatively low or almost no M1 receptor expressed in CHO cells, but high in M1-CHO cells since its agonist (oxotremorine M) but not its antagonist (telenzepine) results in significantly larger responses in M1-CHO cells.

Figure 16:
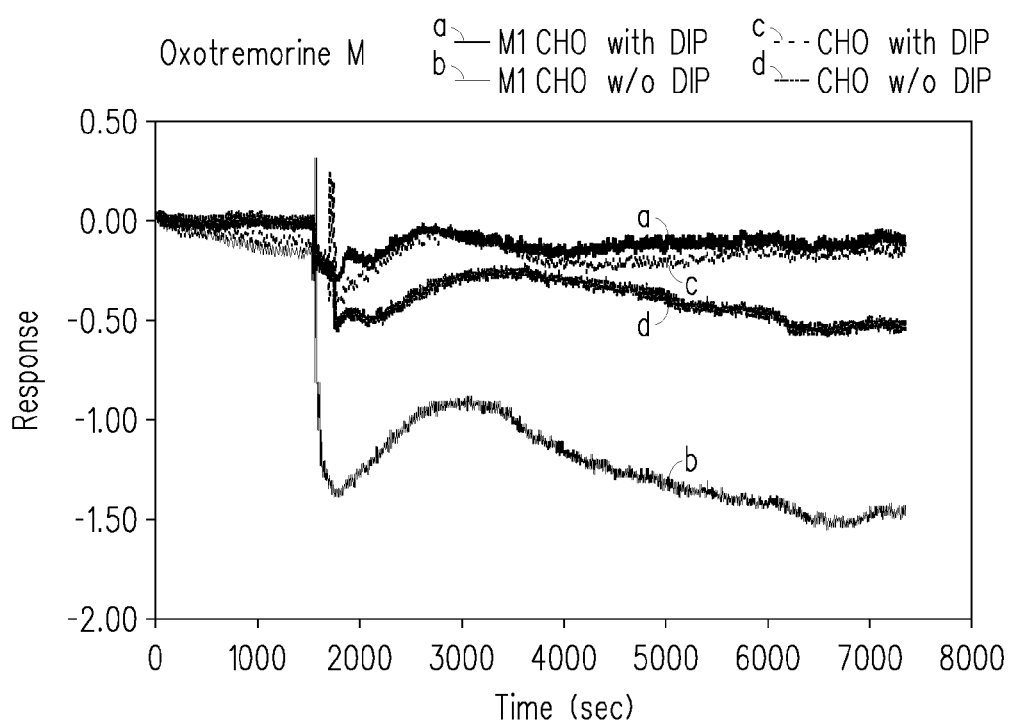

FIG. 16 is a graph that shows the results from an experiment which indicates the effect of pre-incubation of a dynamin phosphorylation inhibitor (dynamin inhibitory peptide, DIP) on oxotremorine M-induced time-dependent response of a monolayer of living CHO cells 108 without and with stably overexpressed rat muscarinic receptor subtype 1 (M1CHO) on wave-guide biosensors 104. Results show that the pre-incubation of cells with DIP almost totally eliminates the oxotremorine M-induced mass distribution responses in both cell lines, suggesting that oxotremorine M-induced mass distribution is dynamin-dependent. The dynamin-dependency is common for most of agonist-induced GPCR translocation.

Figure 17:
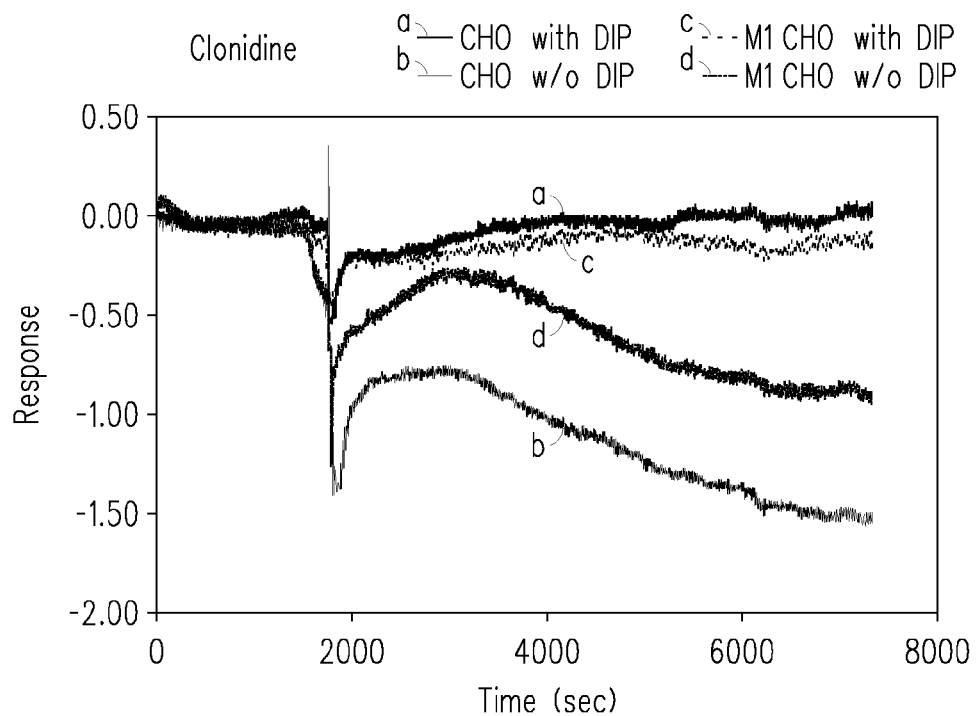

FIG. 17 is a graph that shows the results from an experiment which indicates the effect of pre-incubation of a dynamin phosphorylation inhibitor (dynamin inhibitory peptide, DIP) on clonidine-induced time-dependent response of a monolayer of living Chinese Hamster Ovary (CHO) cells without and with stably overexpressed rat muscarinic receptor subtype 1 (M1CHO) on wave-guide biosensors 104. Results show that the pre-incubation of both cell lines with DIP almost totally eliminates the clonidine-induced mass distribution response, suggesting that clonidine-induced mass distribution is also dynamin-dependent.

Figure 18:
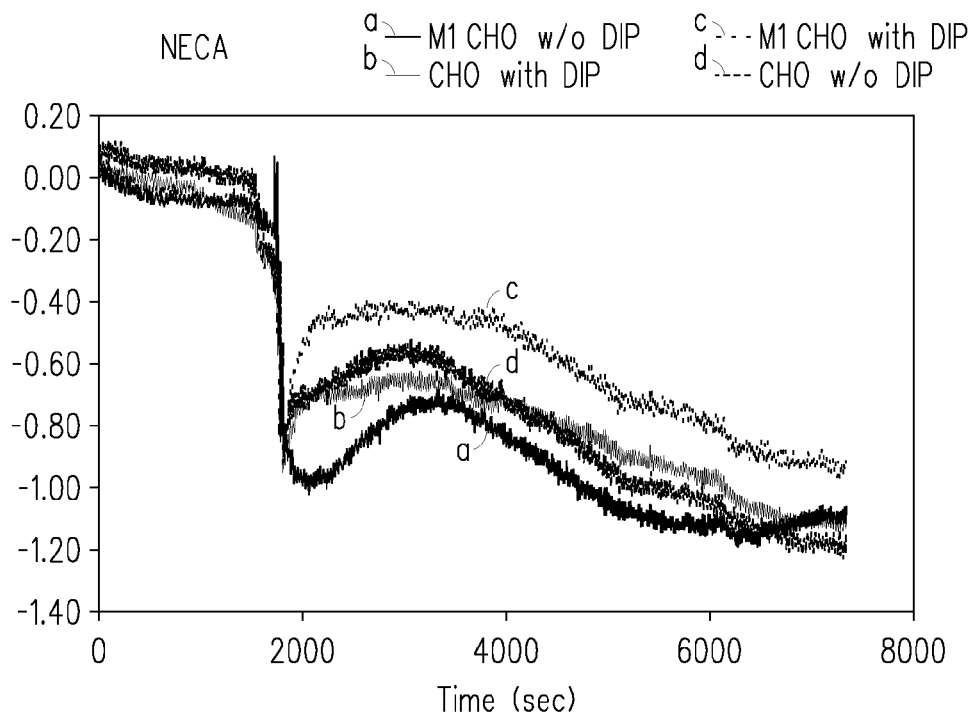
FIG. 18 is a time-dependent LID response of two types of cells (CHO and M1 CHO) before and after addition of NECA (10 µM). Before the compound addition, the cells are pre-incubated either HBSS buffer (Invitrogen) (referred to "without DIP") or with dynamin inhibitory peptide (DIP) at a concentration of 50 µM for 45 minutes.

FIG. 18 is a graph that shows the results from an experiment which indicates the effect of pre-incubation of a dynamin phosphorylation inhibitor (dynamin inhibitory peptide, DIP) on NECA-induced time-dependent response of a monolayer of living CHO cells 108 without and with stably overexpressed rat muscarinic receptor subtype 1 (M1CHO) on wave-guide biosensors 104. Results showed that the pre-incubation of both cells with DIP has little effect on NECA-induced response, suggesting that NECA results in mass redistribution signals in both cell lines through a dynamin-independent pathway.

Some additional features and advantages of using the optical LID system 100 of the present invention are as follows:

(1) The present invention discloses a real time method that can be used to perform a label free functional GPCR cell-based assay which enables compound screening and profiling. This method allows one to study an endogenous but relatively highly expressed GPCR in living cells without needing to genetically engineer the cell to over-express a receptor of interest.

(2) The present invention discloses methods to perform multiplexed cell-based assays using a single sensor which offers an advantage of increased throughput.

(3) The preferred optical LID biosensor 104 is a SPR sensor 104 or a waveguide grating based sensor 104. Other optical-based biosensors can also be used such as ellipsometry devices, evanescent wave devices, and reflectometry devices. For a more detailed discussion about the structure and operation of these two types of optical LID biosensors 104 reference is made to the following documents:

U.S. Pat. No. 4,815,843 entitled "Optical Sensor for Selective Detection of Substances and/or for the Detection of Refractive Index Changes in Gaseous, Liquid, Solid and Porous Samples".

K. Tiefenthaler et al. "Integrated Optical Switches and Gas Sensors" Opt. Lett. 10, No. 4, April 1984, pp. 137-139.

The contents of these documents are incorporated by reference herein.

Although several embodiments of the present invention have been illustrated in the accompanying Drawings and described in the foregoing Detailed Description, it should be understood that the invention is not limited to the embodiments disclosed, but is capable of numerous rearrangements, modifications and substitutions without departing from the spirit of the invention as set forth and defined by the following claims.

What is claimed is:

1. A method for performing a living cell assay, said method comprising the steps of:
   providing a microplate with a well containing a waveguide grating-based biosensor;
   placing a cell medium with a first living-cell type within the well to cover the waveguide grating-based biosensor;
   culturing the first living-cell type on the surface of the waveguide grating-based biosensor;
   applying a solution containing a known agonist or antagonist compound of a specific receptor into the cell medium located on the surface of the waveguide grating-based biosensor;
   interrogating the waveguide grating-based biosensor such that an evanescent electromagnetic field extends into the first living-cell type which enables a time dependent response to be obtained, where the time dependent response indicates a mass redistribution response within the first living-cell type; and
   analyzing the mass redistribution response to determine if a specific receptor has been expressed in the first living-cell type.

2. A method for performing a living cell assay, said method comprising the steps of:
   providing a microplate containing an array of wells, each well incorporating a waveguide grating-based LID biosensor;
   placing a first type of the living cells in a cell medium to cover at least one of the LID biosensors so the first type of the living cells attach to the surface of the at least one LID biosensor;
   placing a second type of the living cells in a cell medium to cover at least one of the remaining uncovered LID biosensors so the second type of the living cells attach to the surface of the at least one remaining uncovered LID biosensor;
   applying a solution containing a compound into the cell medium located on the surfaces of the LID biosensors; and
   interrogating the LID biosensors to obtain time dependent responses which indicate mass redistribution responses within the first type of living cells and the second type of living cells; and
   analyzing the mass redistribution responses to determine if a specific receptor has been expressed in each of the first and second type of living cells.

3. The method of claim 2, wherein the interrogating step further includes interrogating the LID biosensors such that evanescent electromagnetic fields extend into the first type of living cells and the second type of living cells which enables the time dependent response to be obtained, where the time dependent responses indicate the mass redistribution responses within the first type of living cells and the second type of living cells.

4. The method of claim 2, wherein the first cell type and second cell type are identical except for a difference in the ability to express a specific receptor.

5. The method of claim 2, wherein applying a solution containing a compound into the cell medium comprises adding the compound to the cell medium having the first and second cell types spatially separated in different areas in the same well, or having the first and second cell types physically separated in a different well.

* * * * *